United States Patent [19]

Sheppard et al.

[11] Patent Number: 5,567,711

[45] Date of Patent: Oct. 22, 1996

[54] INDOLE-3-CARBONYL AND INDOLE-3-SULFONYL DERIVATIVES AS PLATELET ACTIVATING FACTOR ANTAGONISTS

[75] Inventors: George S. Sheppard, Wilmette; Steven K. Davidsen; James B. Summers, both of Libertyville; George M. Carrera, Jr., Des Plaines, all of Ill.

[73] Assignee: Abbott Laboratories, Abbott Park, Ill.

[21] Appl. No.: 424,911

[22] Filed: Apr. 19, 1995

[51] Int. Cl.⁶ .................... C07D 471/04; A61K 31/445
[52] U.S. Cl. .................... 514/303; 514/234.2; 514/256; 544/127; 544/333; 546/118
[58] Field of Search .................... 546/118; 514/303, 514/234.2, 256; 544/127, 133

[56] References Cited

FOREIGN PATENT DOCUMENTS 9214734  1/1992  WIPO .

*Primary Examiner*—Cecilia Tsang
*Assistant Examiner*—Richard S. Myers, Jr.
*Attorney, Agent, or Firm*—Mona Anand; Jerry F. Janssen

[57] ABSTRACT

The present invention provides compounds of formula

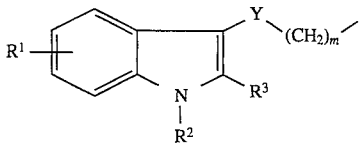

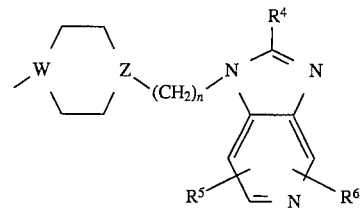

and the pharmaceutically acceptable salts thereof which are potent antagonists of PAF and are useful in the treatment of PAF-related disorders including asthma, shock, respiratory distress syndrome, acute inflammation, transplanted organ rejection, gastrointestinal ulceration, allergic skin diseases, delayed cellular immunity, parturition, fetal lung maturation, and cellular differentiation.

7 Claims, No Drawings

INDOLE-3-CARBONYL AND INDOLE-3-SULFONYL DERIVATIVES AS PLATELET ACTIVATING FACTOR ANTAGONISTS

TECHNICAL FIELD

This invention relates to compounds having pharmacological activity, to compositions containing these compounds, and to a medical method of treatment employing the compounds and compositions. More particularly, this invention concerns certain indole-3-carbonyl and indole-3-sulfonic acid derivatives and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

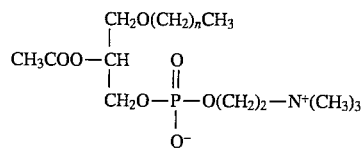

where n is 15 or 17.

PAF is physiologically active and causes contraction of the airway smooth muscle, increased vascular permeability, platelet aggregation, hypotension, and the like. It is now recognized as a powerful mediator of inflammation and may play a physiological or pathobiological role in a variety of clinical conditions, such as asthma and pulmonary dysfunction, acute inflammation, transplanted organ rejection, shock, thrombosis, anaphylaxis, gastrointestinal ulceration, allergic skin diseases, retinal and corneal diseases, chemically induced liver cirrhosis, and ovimplantation in pregnancy. Accordingly, compounds possessing PAF antagonistic effects should be of value in the treatment of any of the above conditions.

SUMMARY OF THE INVENTION

The present invention provides, in its principal aspect, compounds having PAF antagonist activity of formula I:

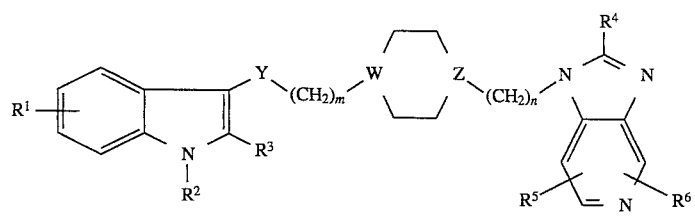

or a pharmaceutically acceptable salt thereof wherein $R^1$ is one or more groups independently selected from the group consisting of (a) hydrogen, (b) halogen, (c) hydroxy, (d) cyano, (e) alkyl of one to six carbon atoms, (f) alkenyl of two to six carbon atoms, (g) alkynyl of two to six carbon atoms, (h) alkoxy of one to six carbon atoms, (i) alkanoyl of one to seven carbon atoms, (j) —COOR$^7$, wherein $R^7$ is hydrogen, alkyl of one to ten carbon atoms, or phenylalkyl wherein the alkyl portion is of one to four carbon atoms, (k) unsubstituted phenyl, (l) phenyl, substituted with alkyl of one to six carbon atoms, alkoxy of one to six carbon atoms, halogen, —NR$^8$R$^9$, where R$^8$ and R$^9$ are independently selected from hydrogen and alkyl of one to six carbon atoms, or R$^8$ and R$^9$ together with the nitrogen atom to which they are attached form a pyrrolidinyl, piperidinyl, piperazinyl, or morpholinyl ring, —COOR$^7$, —C(O)NR$^8$R$^9$, or —SO$_2$NR$^8$R$^9$, (m) —C(O)NR$^8$R$^9$, (n) —OC(O)NR$^8$R$^9$, (o) —NHC(O)NR$^8$R$^9$, (p) 2- or 3-furyl, (q) 2- or 3-thienyl, (r) 2-, 4-, or 5-thiazolyl, (s) 2-, 3-, or 4-pyridyl, (t) 2-, or 4-pyrimidyl, (u) phenylalkyl in which the alkyl portion is of one to six carbon atoms, (v) phenylalkyl, in which the alkyl portion is of one to six carbon atoms and the phenyl moiety is substituted with halogen, alkyl of from one to six carbon atoms, or alkoxy of from one to six carbon atoms, (w) unsubstituted benzoyl, (x) benzoyl substituted with halogen, alkyl of from one to six carbon atoms, or alkoxy of from one to six carbon atoms, (y) unsubstituted phenoxy, (z) phenoxy substituted with halogen, alkyl of from one to six carbon atoms, or alkoxy of from one to six carbon atoms, (aa) unsubstituted phenylalkyloxy, in which the alkyl portion is of one to six carbon atoms, (bb) phenylalkyloxy in which the alkyl portion is of one to six carbon atoms and the phenyl moiety is substituted with halogen, alkyl of from one to six carbon atoms, or alkoxy of from one to six carbon atoms, (cc) unsubstituted phenylalkanoyl, in which the alkanoyl portion is of one to seven carbon atoms, and (dd) phenylalkanoyl, in which the alkanoyl portion is of one to seven carbon atoms and the phenyl moiety is substituted with halogen, alkyl of from one to six carbon atoms, or alkoxy of from one to six carbon atoms.

$R^2$ is selected from the group consisting of (a) hydrogen, (b) alkyl of one to six carbon atoms; (c) —(CH$_2$)$_p$COOR$^7$, where p is 0, 1, 2, 3, or 4, (d) —(CH$_2$)$_q$NR$^8$R$^9$, where q is 2, 3, or 4, (e) (CH$_2$)$_p$COR$^7$ (f) —(CH$_2$)$_p$OR$^7$, (g) —(CH$_2$)$_p$SO$_2$R$^7$, (h) —(CH$_2$)$_p$SO$_2$NR$^8$R$^9$, (i) —(CH$_2$)$_p$CONR$^{10}$R$^{11}$, where R$^{10}$ and R$^{11}$ are independently selected from the group consisting of hydrogen, alkyl of one to six carbon atoms, —(CH$_2$)$_r$COOR$^7$, where r is 1, 2, 3, or 4, —(CH$_2$)$_r$NR$^8$R$^9$, —(CH$_2$)$_r$OH, —(CH$_2$)$_r$SO$_2$R$^7$, and —(CH$_2$)$_r$SO$_2$NR$^8$R$^9$, or R$^{10}$ and R$^{11}$ taken together define a pyrrolidine, morpholine, or thiomorpholine ring, (j) —(CH$_2$)$_p$CN, (k) —(CH$_2$)$_p$-1H-tetrazol-5-yl, (l) —CONHNH$_2$, (m) unsubstituted phenylalkyl wherein the alkyl portion is of one to four carbon atoms, and (n) phenylakyl wherein the alkyl portion is of one to four carbon atoms and the phenyl moiety is substituted with is halogen, alkyl of from one to six carbon atoms, or alkoxy of from one to six carbon atoms.

$R^3$ is selected from hydrogen and alkyl of one to six carbon atoms, Y is selected from the group consisting of >C=O, and >S(O)$_t$, wherein t is 1 or 2, and W and Z are independently CH or N.

$R^4$ is selected from the group consisting of (a) alkyl of one to six carbon atoms, (b) alkenyl of two to six carbon atoms, (c) alkynyl of two to six carbon atoms, (d) alkoxy of one to six carbon atoms, (e) alkylthio of one to six carbon atoms, (f) alkoxyalkyl in which the alkoxy and alkyl portions are independently of one to six carbon atoms, (g) alkylthioalkyl in which the alkyl portions each independently of one to six carbon atoms, (h) haloalkyl of one to six carbon atoms, (i) unsubstituted phenylalkyl wherein the alkyl portion is of one to six carbon atoms, (j) phenylalkyl wherein the alkyl portion io of one to six carbon atoms and the phenyl is substituted with alkyl of one to six carbon atoms, haloalkyl of one to six carbon atoms, alkoxy of one to six carbon atoms, hydroxy, or halogen, (k) cycloalkyl of three to eight carbon atoms, (l) unsubstituted thiophenyl, and (m) thiophenyl substituted with alkyl of one to six carbon atoms, haloalkyl of one to six carbon atoms, alkoxy of one to six carbon atoms, hydroxy, or halogen.

$R^5$ and $R^6$ are independently selected from the group consisting of hydrogen, alkyl of one to six carbon atoms, halogen, haloalkyl, and alkoxy of one to six carbon as atoms, m is 0 or 1, and n is 0, 1, or 2, provided that when Z is nitrogen, n cannot be zero or one.

Compounds of the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

In another aspect, the present invention provides pharmaceutical compositions useful for the treatment of PAF-mediated disorders comprising a therapeutically effective amount of a compound of formula I above in combination with a pharmaceutically acceptable carder.

In another aspect, the present invention provides a method of inhibiting PAF activity by administering to a host mammal in need of such treatment an effective amount of a PAF-inhibiting compound having structure I above.

In yet another aspect of the present invention, there is provided a method of treating PAF-mediated disorders including asthma, shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION OF THE INVENTION

Definitions of Terms

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkylthioalkyl" refers to an alkylthio group, as defined above, attached to the parent molecular moiety through an alkylene group and includes such examples as methylthiomethyl, ethylthiomethyl, propylthiomethyl, n-, sec- and tert-butylthiomethyl and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety, Representative alkoxyalkyl groups include methoxymethyl, methoxyethyl, ethoxyethyl, and the like.

The term "alkoxycarbonyl" represents an ester group; i.e. an alkoxy group attached to the parent molecular moiety through a carbonyl group. Representative examples include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include —C≡C—, —C≡C—CH$_2$—, —C≡C—CH(CH$_3$)—, and the like.

The term "cycloalkyl" denotes a monovalent group derived from a monocyclic or bicyclic saturated carbocylic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated as carbocyclic hydrocarbon by the removal of two hydrogen atoms, for example cyclopentylene, cyclohexylene, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "phenoxy" refers to a phenyl group attached to the parent molecular moiety through an oxygen atom.

The term "phenylalkyloxy" refers to a pheny group attached to the parent molecular moiety through an alkylene group and thence through an oxygen atom. Representative phenylalkyloxy groups include phenylmethoxy, phenylethy-2-yloxy, phenylprop-3-yloxy, phenylprop-2-yloxy, and the like.

The term "phenylalkanoyl" as used herein refers to a pheny group attached to the parent molecular moiety through an alkyl group and thence through a carbonyl group.

The term "thiophenyl" refers to a phenyl group attached to the parent molecular moiety through a sulfur atom.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

The terms "PAF-related disorders" and "PAF-mediated disorders" are used herein to mean disorders related to PAF or mediated by PAF, including asthma, shock, respiratory distress syndromes, acute inflammation, gastric ulceration, transplant organ rejection, psoriasis, allergic skin disease, ischemia and reperfusion injury, delayed cellular immunity, parturition, fetal lung maturation, and cellular differentiation.

PREFERRED EMBODIMENTS

In a preferred embodiment, the compounds of this invention are represented by formula I wherein $R^1$ is one or more groups independently selected from the group consisting of (a) hydrogen, (b) halogen, (c) alkyl of one to six carbon atoms, (d) alkynyl of two to four carbon atoms, (e) alkoxy of one to six carbon atoms, (f) phenyl, optionally substituted with alkyl of one to six carbon atoms, alkoxy of one to is six carbon atoms, or halogen, (f) —COOR$^7$, wherein $R^7$ is hydrogen, alkyl of one to ten carbon atoms, or phenylalkyl wherein the alkyl portion is of one to four carbon atoms, (g) —C(O)NR$^8$R$^9$, (h) —OC(O)NR$^8$R$^9$, (i) 2- or 3-furyl, and (j) 2- or 3-thienyl; $R^2$ is defined above; $R^3$, $R^5$, and $R^6$ are hydrogen; Y is >C=O or >S(O)$_2$; and $R^4$ is alkyl of one to six carbon atoms.

In a more preferred embodiment, the compounds of this invention are represented by formula 1 wherein $R^2$ is selected from the group consisting of (a) —CONR$^{10}$R$^{11}$, where $R^{10}$ and $R^{11}$ are independently selected from hydrogen and alkyl of one to six carbon atoms, and (b) —(CH$_2$)$_q$OR$^7$, wherein q is 2, 3, or 4, and $R^7$ is alkyl of one to four carbon atoms; and Y, $R^1$, $R^3$, $R^4$, $R^5$, and $R^6$ are defined immediately above.

In a still more preferred embodiment, the compounds of this invention are represented by formula I wherein W is N and Y, $R^1$, $R^2$, $R^3$, $R^4$, $R^5$, and $R^6$ are defined immediately above.

In the most preferred embodiment, the compounds of this invention are represented by formula I wherein W is CH or N; Z is CH; m is 0 or 1; n is 0, or 1, provided that m and n are not both 0 or 1; and Y, $R^1$, $R^2$, $R^3$, $R^4$, $R^5$, and $R^6$ are defined immediately above.

Compounds contemplated as falling within the scope of the present invention include, but are not limited to:

6-(4-fluorophenyl)-3-{[4-(1H-2-methylimidazo[4.5-c]pyrid-1-yl)piperidin-1 -yl]carbonyl}indole-1-carboxylic acid dimethyl amide, 6-(4-fluorophenyl)-3-{[4-(1H-2-methylimidazo[4.5-c]pyrid-1-yl)piperidin-1-yl]carbonyl}indole, 3-{[4-(1H-2-methylimidazo[4.5-c]pyrid-1-yl)piperidin-1-yl]carbonyl}indole, 3-{[4-(1H-2-methylimidazo[4.5-c]pyrid-1-yl)piperidin-1-yl]carbonyl}indole-1,4-dicarboxylic acid 1-dimethyl amide-4-methyl ester, 3-{[4-(1H-2-methylimidazo[4.5-c]pyrid-1-yl)methylpiperidin-1-yl]carbonyl}indole-1,4-dicarboxylic acid 1-dimethyl amide-4-methyl ester, 6-(4-fluorophenyl)-3-{[4-(1H-2-methylimidazo[4.5-c]pyrid-1-yl)methylpiperidin-1-yl]carbonyl}indole-1-carboxylic acid dimethyl amide, 4-chloro-3-{[4-(1H-2-methylimidazo[4.5-c]pyrid-1-yl)methylpiperidin-1-yl]carbonyl}indole-1-carboxylic acid dimethyl amide, 1-(2-ethoxyethyl)-6-(4-fluorophenyl)-3-{[4-(1H-2-methylimidazo[4.5-c]pyrid-1-yl)methylpiperidin-1-yl]carbonyl}indole, 1-(2-ethoxyethyl)-4-chloro-3-{[4-(1H-2-methylimidazo[4.5-c]pyrid-1 -yl)methylpiperidin-1-yl]carbonyl}indole, 3-[{4-[(2-(1H-2-methylimidazo[4.5-c]pyrid-1-yl)ethyl]piperazin-1-1-yl}carbonyl]indole-1,4-dicarboxylic acid 1-dimethyl amide 4-methyl ester, 6-(4-fluorophenyl)-3-[{4-[(2-(1H-2-methylimidazo[4.5-c]pyrid-1-yl)ethyl]piperazin-1-yl}carbonyl]indole-1-carboxylic acid dimethyl amide, 6-(4-fluorophenyl)-3-{[4-(1H-2-methylimidazo[4.5-c]pyrid-1-yl)piperidin-1-yl]sulfonyl}indole-1-carboxylic acid t-butyl ester, 6-(4-fluorophenyl)-3-{[4-(1H-2-methylimidazo[4.5-c]pyrid-1-yl)piperidin-1-yl]sulfonyl}indole, 6-(4-fluorophenyl)-3-{[4-(1H-2-methylimidazo[4.5-c]pyrid-1 -yl]sulfonyl}indole-1-carboxylic acid dimethyl amide, 6-(4-fluorophenyl)-3-{[4-(1H-2-methylimidazo[4.5-c]pyrid-1-yl)methylpiperidin-1-yl]sulfonyl}indole-1-carboxylic acid t-butyl ester, 6-(4-fluorophenyl)-3-{[4-(1H-2-methylimidazo[4.5-c]pyrid-1-yl)methylpiperidin-1-yl]sulfonyl}indole, 6-(4-fluorophenyl)-3-{[4-(1H-2-methylimidazo[4.5-c]pyrid-1-yl)methylpiperidin-1-yl]sulfonyl}indole-1-carboxylic acid dimethyl amide, 6-(4-fluorophenyl)-3-[{4-[(2-(1H-2-methylimidazo[4.5-c]pyrid-1-yl)ethyl]piperazin-1-yl}sulfonyl]indole-1-carboxylic acid dimethyl amide, 6-(4-fluorophenyl)-3-{[4-(1H-2-methylimidazo[4.5-c]pyrid-1-yl)piperidin-1 -yl]acetyl}indole, 6-(4-fluorophenyl)-3-{[4-(1H-2-methylimidazo[4.5-c]pyrid-1-yl)piperidin-1-yl]acetyl}indole-1-carboxylic acid dimethyl amide, 3-{[4-(1H-2-methylimidazo[4.5-c]pyrid-1-yl)piperidin-1-yl]acetyl}indole-4-carboxylic acid methy ester, 3-{[4-(1H-2-methylimidazo[4.5-c]pyrid-1-yl)piperidin-1-yl]acetyl}indole-1,4-dicarboxylic acid 1-dimethyl amide 4-methyl ester, 1-(2-ethoxyethyl)-3-{[4-(1H-2-methylimidazo[4.5-c]pyrid-1-yl)piperidin-1-yl]acetyl}indole-1-carboxylic acid methyl ester, 4-chloro-3-{[4-(1H-2-methylimidazo[4.5-c]pyrid-1-yl)piperidin-1-yl]acetyl}indole, 1-(2-ethoxyethyl)-4-chloro-3-{[4-(1H-2-methylimidazo[4.5-c]pyrid-1 -yl)piperidin-1-yl]acetyl}indole, 4-chloro-3-{[4-(1H-2-methylimidazo[4.5-c]pyrid-1-yl)piperidin-1-yl]acetyl}indole-1-carboxylic acid dimethyl amide, 4-methyl-3-{[4-(1H-2-methylimidazo[4.5-c]pyrid-1-yl)piperidin-1-yl]acetyl}indole, 1-(2-ethoxyethyl)-4-methyl-3-{[4-(1H-2-methylimidazo[4.5-c]pyrid-1 -yl)piperidin-1-yl]acetyl}indole, 4-methyl-3-{[4-(1H-2-methylimidazo[4.5-c]pyrid-1-yl)piperidin-1-yl]acetyl}indole-1-carboxylic acid dimethyl amide, 3-{[trans-4-[(1H-2-methylimidazo[4.5-c]pyrid-1-yl)methylcyclohex-1-yl]carbonyl}indole-1,4-dicarboxylic acid 1-dimethyl amide, 4-(fur-2-yl)-3-{[4-(1H-2-methylimidazo[4.5-c]pyrid-1-yl)methylpiperidin-1-yl]carbonyl}indole-1-carboxylic acid, 4-(thien-2-yl)-3-{[4-(1H-2-methylimidazo[4.5-c]pyrid-1-yl)methylpiperidin-1 -yl]carbonyl}indole-1-carboxylic acid, 4-ethynyl-3-{[4-(1H-2-methylimidazo[4.5-c]pyrid-1-yl)methylpiperidin-1-yl]carbonyl}indole-1-carboxylic acid, 4-methoxy-3-{[4-(1H-2-methylimidazo[4.5-c]pyrid-1-yl)methylpiperidin-1-yl]carbonyl}indole-1-carboxylic acid dimethyl amide, 4-(N,N-dimethylaminocarbonyloxy)-3-{[4-(1H-2-methylimidazo[4.5-c]pyrid-1 -yl)methylpiperidin-1-yl]carbonyl}indole-1-carboxylic acid dimethyl amide, and 4-(N,N-dimethylaminocarbonylamino)-3-{[4-(1H-2-methylimidazo[4.5-c]pyrid-1 -yl)methylpiperidin-1-yl]carbonyl}indole-1-carboxylic acid dimethyl amide.

PAF Inhibitory Activity of the Compounds of the Present Invention

The ability of representative compounds of the present invention to inhibit PAF activity was determined in an in vitro test using the following method.

Citrated whole rabbit blood was obtained from Pel-Freez (Rogers, Ark.). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM $MgCl_2$/2 mM EDTA (TME buffer, pH 7.0) with 0.25M sucrose added for membrane stabilization.

The standard PAF receptor binding assay contained 10 μg platelet membrane protein, 0.6 nM $[^3H]C_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Milliliter-GV® (Millipore Corp.) filtration plates; incubation time was for 60 minutes at room temperature (22°–23° C.). "Specific binding" was operationally defined as the arithmetic difference between "total binding" of 0.6 nM $[^3H]C_{18}$-PAF (in the absence of added PAF) and "nonspecific binding" (in the presence of 1 μM PAF). After the prescribed incubation, platelet membranes were filtered under vacuum and washed with 1 milliliter of "binding buffer". The filters were dried and removed. The bound radioactivity was quantitated with a Berthold TLC-Linear Analyzer model LB2842.

Dose-response curves of inhibition of specific $[^3H]C_{18}$-PAF binding by test compounds were conducted in triplicate, with at least four doses covering the active range. Experiments were repeated at least once. $IC_{50}$ values (concentration producing 50% inhibition) were determined by point-to-point evaluation. $K_i$ values of inhibitory binding constants were calculated according to the method of Cheng and Prusoff [Biochem. Pharmacol. 22 (1973) 3099–3108] whereby $$K_i = \frac{IC_{50}}{1 + ([[^3H]PAF]/K_d\,[^3H]PAF)}$$

$$= \frac{IC50}{1 + (0.6\,nM/0.6\,nM)}$$

$$= \frac{IC50}{2}$$

The values of $K_i$ for representative compounds of the present invention appear in Table 1.

TABLE 1

| Example | $K_i$ (nM) or % inhibition |
|---|---|
| 1 | 3.3 |
| 2 | 44 |
| 3 | 100 |
| 4 | 140 |
| 5 | 74 |
| 6 | 2.5 |
| 7 | 18 |
| 8 | 1.2 |
| 9 | 29 |
| 10 | 200 |
| 11 | 30 |
| 12 | 340 |
| 13 | 32% @ 1.0 μM |
| 14 | 120 |
| 15 | 65 |
| 16 | 250 |
| 17 | 1.2 |
| 18 | 110 |
| 19 | 95 |
| 20 | 2.5 |
| 21 | 14 |
| 22 | 12 |
| 23 | 5.2 |
| 24 | 30 |
| 25 | 10 |
| 26 | 12 |
| 27 | 71 |
| 28 | 0.5 |
| 29 | 2.0 |
| 30 | 2.4 |

Pharmaceutical Compositions

The present invention also provides pharmaceutical compositions which comprise one or more of the compounds of formula I above formulated together with one or more non-toxic pharmaceutically acceptable carders. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carders, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drag, it is desirable to slow the absorption of the drug from subcutaneous or intramuscular injection. This may be accomplished by the use of a liquid suspension of crystalline or amorphous material with poor water solubility. The rate of absorption of the drag then depends upon its rate of dissolution which, in turn, may depend upon crystal size and crystalline form. Alternatively, delayed absorption of a parenterally administered drug form is accomplished by dissolving or suspending the drag in an oil vehicle.

Injectable depot forms are made by forming microencapsule matrices of the drag in biodegradable polymers such as polylactide-polyglycolide. Depending upon the ratio of drag to polymer and the nature of the particular polymer employed, the rate of drag release can be controlled. Examples of other biodegradable polymers include poly(orthoesters) and poly(anhydrides). Depot injectable formulations are also prepared by entrapping the drag in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments, and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend as upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

Generally dosage levels of about 0.001 to about 100 mg, more preferably of about 0.01 to about 20 mg, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

Preparation of Compounds of the Invention

The compounds of this invention may be prepared by a variety of synthetic routes. Representative procedures are outlined below. It should be understood that the groups $R^1$, $R^2$, $R^3$, $R^4$, $R^5$, $R^6$, and Z correspond to the groups identified above.

The preparation of compounds in which Y is CO and W is N is outlined in Scheme 1. Standard peptide coupling of Indole-3-carboxylic acid 1, for example using bis(2-oxo-3-oxazolidinyl)phosphinic chloride (BOP-Cl) and amine 2, gives the compounds wherein m=0. The compounds of the invention wherein m=1 are prepared by reaction of chloroacetyl indole 4 with amine 2 in a polar solvent such as N,N-dimethylformamide in the presence of base, for example N,N-diisopropylethylamine, followed by introduction of the group $R^2$ using a base such as NaH or KOH and $R^2X$, where X is a suitable leaving group such as Cl, Br, I, methanesulfonyl, trifluoromethanesulfonyl, or p-toluenesulfonyl.

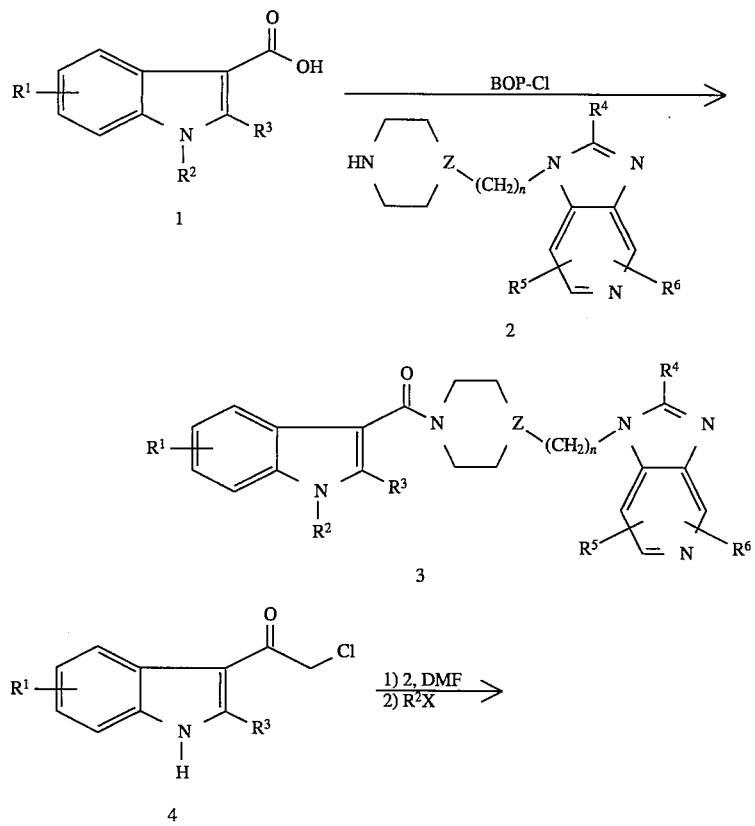

-continued
Scheme 1

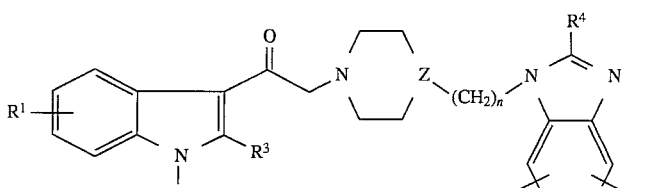

5

The preparation of compounds wherein Y is $SO_2$ and W is N is shown in Scheme 2. Bromoindole 6 is convened to chlorosulfonyl indole 7 by metallation using, for example, t-BuLi, followed by reaction with $SO_2$ gas and N-Chlorosuccinimide. Displacement of Cl with amine 2 in the presence of a base such as triethylamine gives 8. Removal of the tert-butoxycarbonyl group, for example using sodium methoxide, gives 9 which is converted to the desired compound by reaction with base and $R^2X$ as described above.

chloride 12, gives 3-acylindole 13. The group $R^2$ is then introduced by reaction of 13 with base and $R^2X$ as described above to give 14. Removal of the benzyloxycarbonyl group with $H_2$ catalyzed by Palladium on carbon, followed by condensation of the primary amine 15 with 3-nitro-4-ethoxypyridine gives 16. Reduction of the nitro group using, for example $SnCl_2$ gives diamine 17 which is converted to the desired compound 18 by reaction, for example, with $(R^4CO)_2O$ and $R^4CO_2H$ where $R^4$ is alkyl or haloalkyl;

Scheme 2

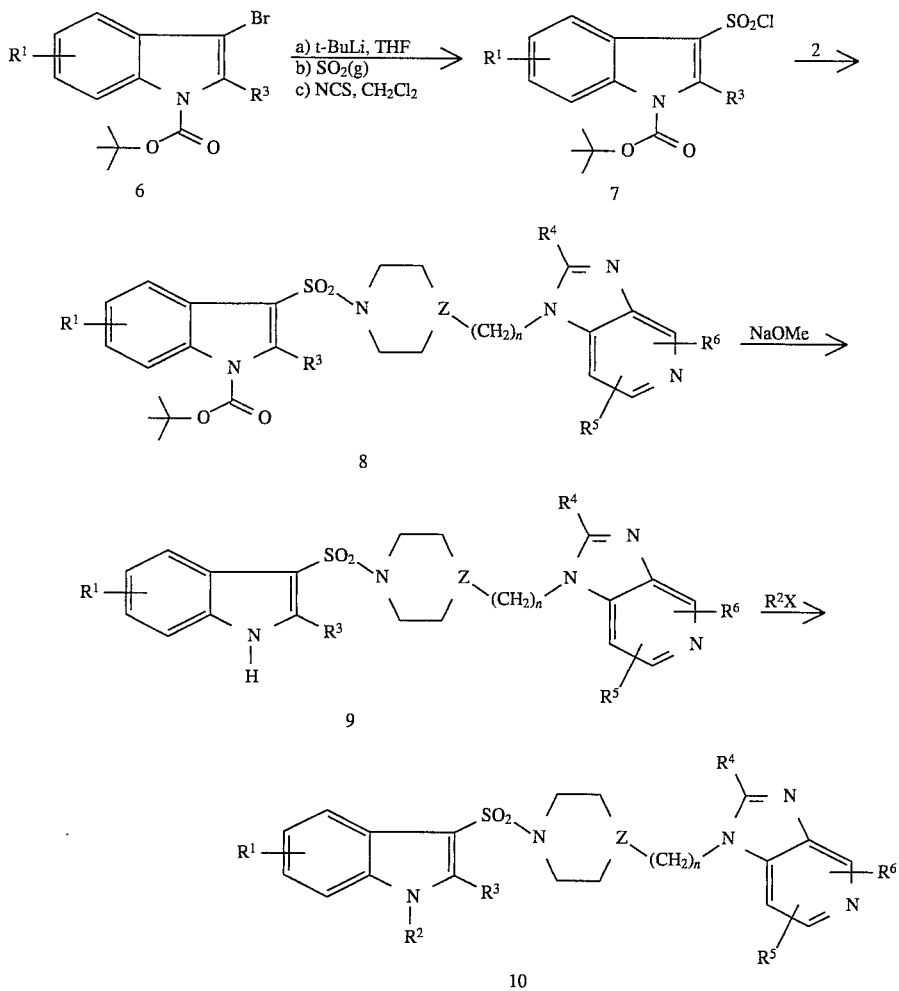

Compounds of the invention wherein W and Z are both CH are prepared as described in Scheme 3. Reaction of Indole 11 with ethylmagnesium bromide, $ZnCl_2$, and acid $R^4COCl$ where $R^4$ is aryl; or ethyl(ethoxymethylene)cyanoacetate where $R^4$ is H.

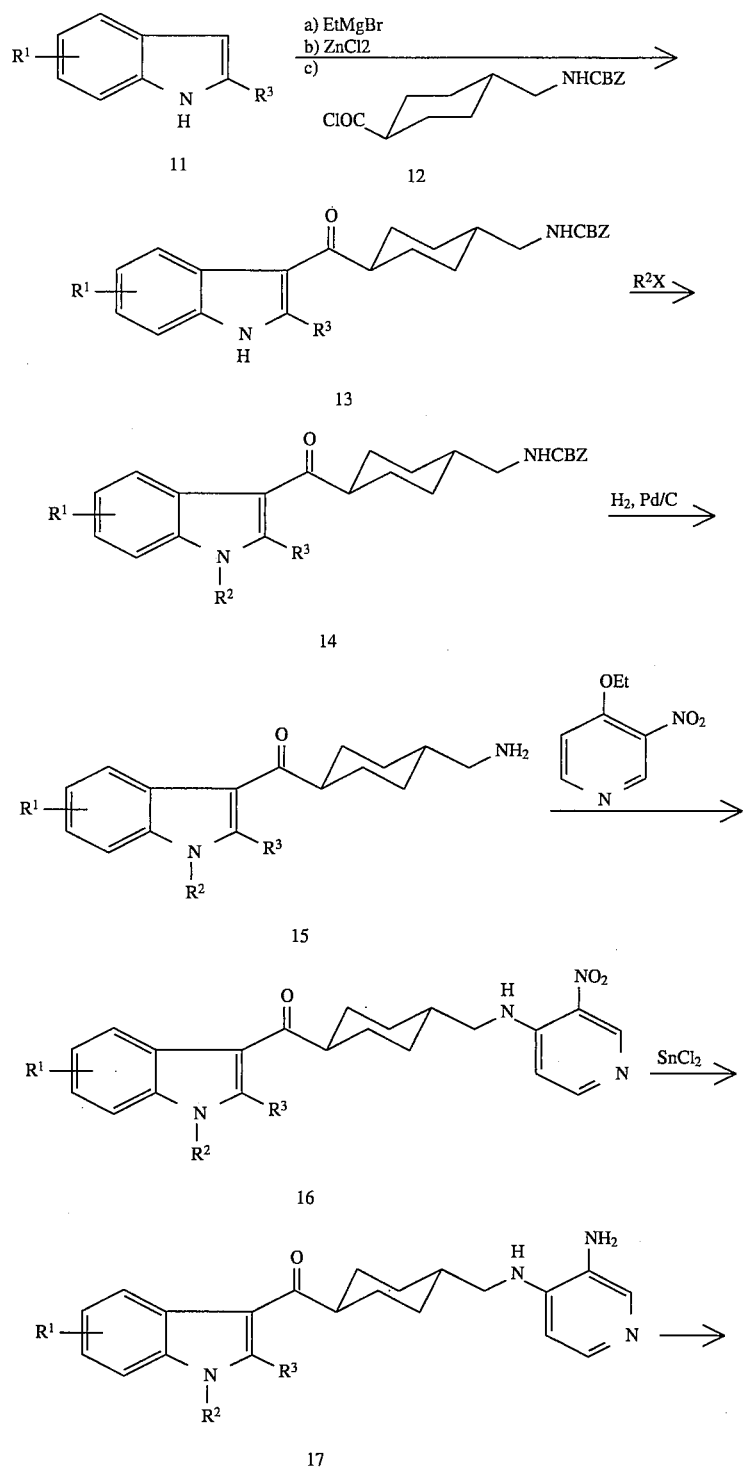
Scheme 3

-continued
Scheme 3

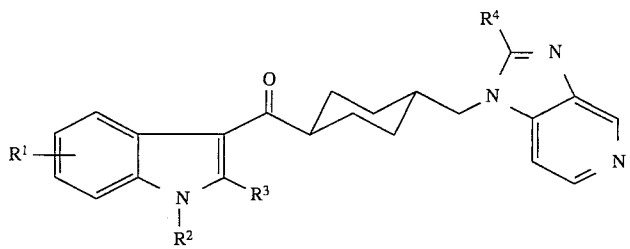

18

Preparation of Amine Intermediates

The preparation of the amines 2 used above is outlined in Scheme 4. Primary amine 19, where P is H or optionally a suitable protecting group such as acetyl or ethoxycarbonyl is condensed with 3-nitro-4-ethoxypyridine to give 20. Reduction of the nitro group, for example by hydrogenolysis catalyzed by palladium on carbon gives diamine 21 which is then converted to 22, for example, with $(R^4CO)_2O$ and $R^4CO_2H$ where $R^4$ is alkyl or haloalkyl; $R^4COCl$ where $R^4$ is aryl; or ethyl(ethoxymethylene)cyanoacetate where $R^4$ is H. Deprotection of 22 using aqueous base such as KOH or LiOH in alcohol gives 2. The preparation of representative amines is outlined below.

Scheme 4

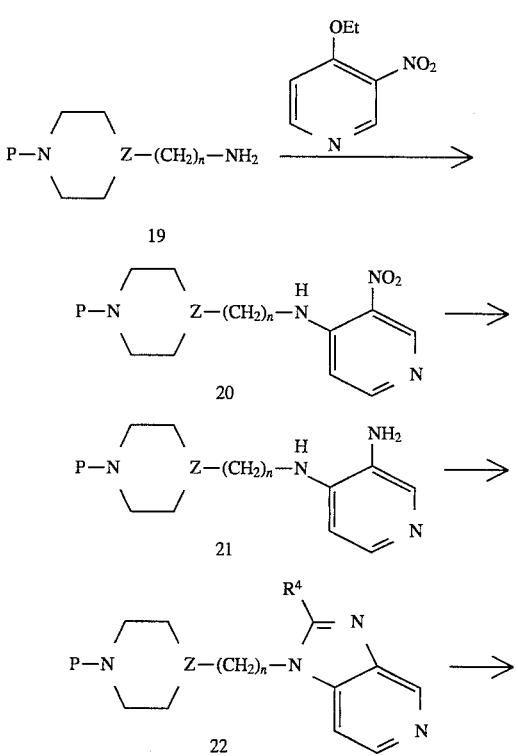

-continued
Scheme 4

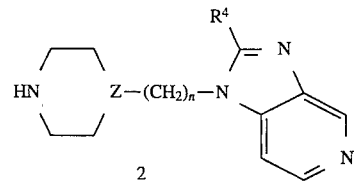

Amine 1

1H-1-(piperidin-4-yl)-2-methyl[4.5-c]imidazopyridine

Step 1: 3-nitro-4-[N-(1-ethoxycarbonylpiperidin-4-yl)]aminopyridine.

A mixture of ethyl 4-amino-1-piperidinecarboxylate (3.53 g, 20.5 mmol) and 4-ethoxy-3-nitropyridine (3.65 g, 21/7 mmol) in $CH_3CN$ (25 mL) was heated at reflux for 40 hours. The reaction mixture was cooled to ambient temperature and concentrated in vacuo to give an orange syrup which was used without further purification.

Step 2: 3,4-[N-(1-ethoxycarbonylpiperidin-4-yl)]diaminopyridine.

Catalytic hydrogenation (10% Pd/C, 1 atm. $H_2$, ethanol) of the 3-nitro-4-[N-(1-ethoxycarbonylpiperidin-4-yl)]aminopyridine prepared in step 1 gave 6.22 g of 3,4-[N-(1-ethoxycarbonylpiperidin-4-yl)]diaminopyridine which was used without further purification.

Step 3: 1H-1-(1-ethoxycarbonylpiperidin-4-yl)-2-methyl [4.5-c]imidazopyridine.

A solution of the 3,4-[N-(1-ethoxycarbonylpiperidin-4-yl)]diaminopyridine (6.22 g) prepared in step 2 in acetic anhydride (50 mL) was heated at reflux for 70 hours. The reaction mixture was cooled to ambient temperature and the acetic anhydride was quenched by slow addition of methanol. The reaction mixture was concentrated in vacuo and the residue partitioned between $CH_2Cl_2$ and saturated aqueous $Na_2CO_3$. The organic phase was concentrated in vacuo. Chromatography on silica gel (1 triethylamine: 3 methanol: 96 $CH_2Cl_2$) gave 1H-1-(1 -ethoxycarbonylpiperidin-4-yl)-2-methyl[4.5-c]imidazopyridine (3.7 g).

Step 4: 1H-1-(piperidin-4-yl)-2-methyl[4.5-c]imidazopyridine

To a solution in 95% ethanol (20 mL) of 1H-1-(1-ethoxycarbonylpiperidin-4-yl)-2-methyl[4.5-c]imidazopyridine (3.7 g, 12.8 mmol), prepared in step 3, was added a solution of powdered KOH (2.47 g, 44 mmol) in $H_2O$ (8 mL). The reaction mixture was heated at reflux for 72 hours. The reaction mixture was cooled to ambient temperature and diluted with $H_2O$ (50 mL). The solution was continuously extracted into $CH_2Cl_2$ for 7 hours. The organic phase was dried over $MgSO_4$, filtered, and concentrated in vacuo to give 1H-1-(piperidin-4-yl)-2-methyl[4.5-c]imidazopyridine (2.07 g) as a yellow solid.

Amine 2

1H-1-(piperidin-4-ylmethyl)-2-methyl[4.5-c]imidazopyridine

Step 1: 1H-1-(1-acetylpiperidin-4-ylmethyl)-2-methyl[4.5-c]imidazopyridine.

The desired compound (3.71 g) was prepared according to the method of Amine 1, steps 1–3, except substituting 4-aminomethylpiperidine for ethyl 4-amino-1-piperidinecarboxylate.

Step 2: 1H-1-(piperidin-4-ylmethyl)-2-methyl[4.5-c]imidazopyridine.

To a solution in absolute ethanol (40 mL) of 1H-1-(1-acetylpiperidin-4-ylmethyl)-2-methyl[4.5-c]imidazopyridine (3.7 g, 13.6 mmol), prepared in step 1, was added a solution of LiOH. $H_2O$ in $H_2O$ (15 mL). The reaction mixture was heated at reflux for 20 hours, then was diluted with brine (100 mL) and continuously extracted into $CH_2Cl_2$ for 20 hours. The organic phase was dried over $MgSO_4$, filtered, and concentrated in vacuo to give 1H-1-(piperidin-4-ylmethyl)-2-methyl[4.5-c]imidazopyridine (2.51 g) as a yellow foam.

Amine 3

1H-1-[2-(piperazin-1-yl)ethyl]-2-methyl[4.5-c]imidazopyridine

The desired compound was prepared according to the method of Amine 1, except substituting 1-(2-aminoethyl)piperazine for ethyl 4-amino-1-piperidinecarboxylate.

Preparation of Indole Intermediates

Indole 1

6-(4-fluorophenyl)indole-1,3-dicarboxylic acid 1-dimethyl amide

Step 1: 6-(4-fluorophenyl)indole-3-carboxaldehyde.

To a solution of DMF (5.0 mL, 64 mmol) and $CH_2Cl_2$ (120 mL) was added oxalyl chloride (2.1 mL, 24 mmol). The mixture was stirred for 45 minutes at ambient temperature and then was decanted into a solution of 6-(4-fluorophenyl)indole (5.1 g, 24 mmol), which was prepared as described in International Application Number PCT/US92/05890 (4 Feb. 1993). The reaction mixture was stirred for 90 minutes at ambient temperature and the imminium salt was isolated by filtration. The solids were dissolved in methanol (150 mL) and saturated aqueous $NaHCO_3$ (200 mL) was added. The resulting precipitate was filtered and dried in a vacuum oven to give 6-(4-fluorophenyl)indole-3-carboxaldehyde (4.14 g, 72%) as a tan powder.

Step 2: 6-(4-fluorophenyl)indole-3-carboxaldehyde-1-carboxylic acid dimethyl amide.

To a solution in THF (175 mL) of 6-(4-fluorophenyl)indole-3-carboxaldehyde (4.14 g, 17.3 mmol), prepared in step 1, was added powdered KOH (5.10 g, 91 mmol). After stirring for 3 minutes N,N-dimethylcarbamyl chloride (1.8 mL, 20 mmol) was added and stirring was continued for 90 minutes. The reaction mixture was diluted with ethyl acetate (1 L) and washed with pH 7 buffer. The organic phase was dried over $MgSO_4$, filtered, and concentrated in vacuo to give 5.22 g of solid which contained about 8% starting material. The above procedure was then repeated to give 6-(4-fluorophenyl)indole-3-carboxaldehyde-1-carboxylic acid dimethyl amide (4.86 g, 91%) as a tan solid.

Step 3: 6-(4-fluorophenyl)indole-1,3-dicarboxylic acid 1-dimethyl amide.

To a solution in THF (25 mL) and tert-butyl alcohol (70 mL) of 6-(4-fluorophenyl)indole-3-carboxaldehyde-1-carboxylic acid dimethyl amide (437 mg, 1.4 mmol), prepared as in step 2, was added 2-methyl-2-butene (2.0M in THF, 8.0 mL, 16 mmol). A solution in $H_2O$ (20 mL) of $NaClO_2$ (1.2 g, 13 mmol) and $NaH_2PO_4$ (2.4 g, 17 mmol) was added dropwise and the reaction mixture was stirred overnight at ambient temperature. The solvents were stripped off in vacuo and $H_2O$ (100 mL) was added to the residue. The pH was adjusted to 3 with concentrated HCl, the $H_2O$ was decanted, and the residue was taken up in ethyl acetate. The organic phase was dried over $MgSO_4$, filtered, and concentrated in vacuo to give a dark-brown oil (0.53 g). The oil was taken up in THF and treated with activated carbon. Filtration and removal of the THF in vacuo gave 6-(4-fluorophenyl)indole-1,3-dicarboxylic acid 1-dimethyl amide (0.43 g, 93%) as a red solid.

Indole 2

6-(4-fluorophenyl)indole-3-carboxylic acid

The desired indole was prepared according to the method of Indole 1, steps 1 and 3.

Indole 3

Indole-1,3,4-tricarboxylic acid 1-dimethyl amide 4-methyl ester

The desired indole was prepared according to the method of Indole 1, except substituting indole-4-carboxylic acid methyl ester for 6-(4-fluorophenyl)indole.

Indole 4

4-chloroindole-1,3-tricarboxylic acid dimethyl amide

The desired indole was prepared according to the method of Indole 1, except substituting 4-chloroindole for 6-(4-fluorophenyl)indole.

Indole 5

6-(4-fluorophenyl)indole-3-sulfonyl chloride

Step 1: 6-(4-fluorophenyl)indole-1-carboxylic acid t-butyl ester.

The desired compound was prepared by treating a solution in $CH_3CN$ of 6-(4-fluorophenyl)indole with di-tert-butyldicarbonate and 4-dimethylaminopyridine.

Step 2: 6-(4-fluorophenyl)-3-bromoindole-1-carboxylic acid t-butyl ester.

To a solution under $N_2$ of 6-(4-fluorophenyl)indole-1-carboxylic acid t-butyl ester (2.00 g, 6.42 mmol), prepared as in step 1, in THF (36 mL) was added N-bromosuccinimide (1.26 g, 7.08 mmol) in a single portion and the clear-orange solution was stirred overnight at ambient temperature. The reaction mixture was diluted with ether (500 mL) and extracted with aqueous NaHSO₃ (1–2M, 250 mL) and saturated aqueous NaHCO₃. The organic phase was dried over Na₂SO₄, filtered, and concentrated in vacuo to give a viscous, clear-yellow oil (2.58 g), which solidified on standing.

Step 3: 1-tert-butoxycarbonyl-6-(4-fluorophenyl)indole-3-sulfonyl chloride.

To a −70° C. solution under N₂ of 6-(4-fluorophenyl)-3-bromoindole-1-carboxylic acid t-butyl ester (1.00 g, 2.56 mmol), prepared as in step 2, in THF (6 mL), was added tert-butyllithium (1.7M in pentane, 3.00 mL, 5.10 mmol). The reaction mixture was stirred for 15 minutes and then SO₂ gas was bubbled into the solution for 5–10 minutes. The clear-orange solution was stirred for 2.5 hours at −60°—70° C., and then was warmed to 0° C. over 4 hours, during which time the excess SO₂ distilled off. Hexane (20 mL) was then added which resulted in formation of a heavy, clear-brown oil. The hexane was decanted and replaced with CH₂Cl₂ (5 mL). The resulting clear-orange solution was cooled in an ice bath and N-chlorosuccinimide (0.53 g, 4.0 mmol) was added. The cold bath was removed and the thick suspension was stirred for 75 minutes. The reaction mixture was diluted with CH₂Cl₂ and shaken with aqueous NaHSO₃ (1–2M, 50 mL). The resulting emulsion was broken with brine, and the organic phase was again shaken with aqueous NaHSO₃, then extracted with brine, dried over Na₂SO₄, filtered, and concentrated in vacuo to give a brown foam (1.13 g). Chromatography on silica gel (20:1, then 10:1 hexane-ethyl acetate) gave 1-tert-butoxycarbonyl-6-(4-fluorophenyl)indole-3-sulfonyl chloride as a pale-yellow oil. Azeotroping with CH₂Cl₂ gave opaque yellow rosettes.

Indole 6

6-(4-fluorophenyl)-3-chloroacetylindole

To a solution under N₂ of 6-(4-fluorophenyl)indole (10.0 g, 47.4 mmol) in dioxane (36 mL) was added pyridine (5.80 mL, 71.8 mmol) and the solution was heated to 60° C. A solution of chloroacetyl chloride (5.66 mL, 71.1 mmol) in dioxane (12.5 mL) was added over one hour. The reaction mixture was stirred for one hour at 60° C., then was cooled to ambient temperature and partitioned between H₂O and ether. The resulting orange precipitate was filtered off, recrystallized from ethanol, and rinsed with cold ether to give 6-(4-fluorophenyl)-3-chloroacetylindole (2.78 g, 20% as an orange solid.

Indole 7

3-chloroacetylindole-4-carboxylic acid methyl ester

To a solution under N₂ of 4-methoxycarbonylindole (9.00 g, 51.4 mmol) in anhydrous CH₂Cl₂ (800 mL) was added ethylmagnesium chloride (3.0M in ether, 17.2 mL, 51.6 mmol) over 10 minutes. The reaction mixture was stirred for 20 minutes and ZnCl₂ (1.0M in ether, 154 mL, 154 mmol) was added all at once and stirring was continued for 20 minutes. A solution of chloroacetyl chloride (4.50 mL, 56.5 mmol) in CH₂Cl₂ (200 mL) was added over 15 minutes and the reaction mixture was stirred for 70 hours at ambient temperature. The reaction mixture was poured into saturated aqueous NH₄Cl, and the aqueous phase was extracted with CH₂Cl₂. The combined organic layers were washed with brine, dried over Na₂SO₄, filtered, and concentrated in vacuo to give a viscous, dark-brown oil (13.6 g). Chromatography on silica gel (1:1, then 2:1 ethyl acetate-hexane) gave 3-chloroacetylindole-4-carboxylic acid methyl ester (6.60 g, 51%) as yellow flakes.

Indole 8

4-chloro-3-chloroacetylindole

The desired compound was prepared according to the method of Indole 7, except substituting 4-chloroindole for 4-methoxycarbonylindole.

Indole 9

4-methyl-3-chloroacetylindole

The desired compound was prepared according to the method of Indole 7, except substituting 4-methylindole for 4-methoxycarbonylindole.

Indole 10

4-bromoindole-1,3-dicarboxylic acid dimethyl amide

The desired indole is prepared according to the method of Indole 1, except substituting 4-bromoindole for 6-(4-fluorophenyl)indole.

Indole 11

4-methoxyindole-1,3-dicarboxylic acid dimethyl amide

The desired indole is prepared according to the method of Indole 1, except substituting 4-methoxyindole for 6-(4-fluorophenyl)indole.

The foregoing may be better understood by the following Examples, which are presented for illustration and are not intended to limit the scope of the invention.

EXAMPLE 1

Preparation of 6-(4-fluorophenyl)-3-{[4-(1H-2-methylimidazo[4.5-c]pyrid-1 -yl)piperidin-1-yl]carbonyl)indole-1-carboxylic acid dimethyl amide hydrochloride.

To a solution in THF (6 mL) of 6-(4-fluorophenyl)indole-1,3-dicarboxylic acid dimethyl amide (indole 1) (0.106 g, 0.33 mmol) was added N,N-diisopropylethylamine (0.1 mL, 0.57 mmol) and bis(2-oxo-3-oxazolidinyl)phosphinic chloride (BOP-Cl) (0.096 g, 0.38 mmol). After 5 minutes, a solution in THF (3 mL) of 1H-1-(piperidin-4-yl)-2-methyl [4.5-c]imidazopyridine (amine 1) (0.100 g, 0.46 mmol) was added and the reaction mixture was stirred for 20 hours at ambient temperature. The reaction mixture was partitioned between CH₂Cl₂ and saturated aqueous NaHCO₃. The organic phase was dried over MgSO₄, filtered, and concentrated in vacuo to give 6-(4-fluorophenyl)-3-{[4-(1H-2-methylimidazo[4.5-c]pyrid-1-yl)piperidin-1-yl] carbonyl}indole-1-carboxylic acid dimethyl amide (0.146 g) as a tan foam. The hydrochloride salt was prepared by treating a solution in ethyl acetate of the free base with 4N HCl/dioxane solution followed by filtration. mp 193°–195° C. ¹H NMR(CDCl₃, 300 MHz) δ9.02 (s, 1H), 8.38 (d, 1H, J=6 Hz), 7.80 (s, 1H), 7.78 (d, 1H, J=6 Hz), 7.60 (m, 3H), 7.52 (m, 1H), 7.39 (m, 1H), 7.16 (m, 2H), 4.52 (m, 1H), 3.20 (m, 2H), 3.16 (s, 6H), 2.71 (s, 3H), 2.46 (m, 2H), 2.03 (m, 2H), 1.50 (m, 2H). IR (microscope) 3400 (br), 3080,2940, 1690, 1615, 1480, 1440, 1390 cm⁻¹. MS (DCI/NH₃) m/e 525 (M+H)⁺. Anal calcd for $C_{30}H_{29}FN_6O_2 \cdot HCl \cdot 3\ H_2O$: C, 58.58; H, 5.90; N, 13.66. Found: C, 58.58; H, 5.72; N, 12.99.

EXAMPLE 2

Preparation of 6-(4-fluorophenyl)-3-{[4-(1H-2-methylimidazo[4.5-c]pyrid-1 -yl)piperidin-1-yl]carbonyl}indole hydrochloride.

The desired compound was prepared according to the method of Example 1, except substituting 6-(4-fluorophenyl)indole-3-carboxylic acid (indole 2) for 1-N,N-dimethylcarbamoyl-6-(4-fluorophenyl)indole-3-carboxylic acid. mp 120°–123° C. ¹H NMR (DMSO-d6, 300MHz) δ9.01 (s, 1H), 8.48 (d, 1H, J=6 Hz), 7.81 (d, 1H, J=8 Hz), 7.70 (d, 1H, J=3 Hz), 7.58 (m, 3H), 7.47 (m, 1H), 7.41 (m, 1H), 7.14 (m, 2H), 4.48 (m, 1H), 3.62 (m, 2H), 3.19 (m, 1H), 2.71 (s, 2H), 2.48 (m, 2H), 2.03 (m, 2H). IR (microscope) 3100 (br), 2980, 2920, 1755, 1605, 1515, 1435 cm⁻¹. MS (DCI/NH₃) m/e 454 (M+H)⁺, 200, 302, 130. Anal calcd for $C_{27}H_{24}FN_5O \cdot 3\ H_2O$: C, 63.89; H, 5.96; N, 13.80. Found: C, 64.18; H, 6.08; N, 12.67.

EXAMPLE 3

Preparation of 3-{[4-(1H-2-methylimidazo[4,5-c]pyrid-1-yl)piperidin-1-yl]carbonyl}indole hydrochloride.

The desired compound was prepared according to the method of Example 1, except substituting indole-3-carboxylic acid for 1-N,N-dimethylcarbamoyl-6-(4-fluorophenyl)indole-3-carboxylic acid. mp 157°–160° C. ¹H NMR (DMSO-d6, 300 MHz) δ11.64 (bds, 1H), 9.39 (s, 1H), 8.58 (d, 1H, J=8 Hz), 8.42 (d, 1H, J=8 Hz), 7.80 (d, 1H, J=3 Hz), 7.78 (d, 1H, J=7 Hz), 7.48 (d, 1H, J=7 Hz), 7.16 (m, 2H), 4.88 (m, 1H), 4.54 (m, 2H), 3.21 (m, 2H), 2.84 (s, 3H), 2.32 (m, 2H), 2.09 (m, 2H). IR (microscope) 3350 (br), 3120 (br), 2620 (br), 1755, 1605, 1525 cm⁻¹. MS (DCI/NH₃) m/e 360 (M+H)⁺, 130. Anal calcd for $C_{21}H_{21}N_5O \cdot 2\ HCl \cdot 1.5\ H_2O$: C, 54.91; H, 5.70; N, 15.25. Found: C, 55.12; H, 5.65; N, 14.45.

EXAMPLE 4

Preparation of 3-{[4-(1H-2-methylimidazo[4.5-c]pyrid-1-yl)piperidin-1-yl]carbonyl}indole-1,4-dicarboxylic acid 1-dimethyl amide-4-methyl ester hydrochloride.

The desired compound was prepared according to the method of Example 1, except substituting indole-1,3,4-tricarboxylic acid 1-dimethyl amide 4-methyl ester (indole 3) for 6-(4-fluorophenyl)indole-1,3-dicarboxylic acid 1-dimethyl amide. mp 190°–193° C. (dec). ¹H NMR (DMSO-d6, 300 MHz) δ9.39 (s, 1H), 8.64 (d, 1H, J=6 Hz), 8.58 (d, 1H, J=6 Hz), 8.07 (s, 1H), 7.90 (dd, 1H, J=0.5, 7 Hz), 7.71 (dd, 1H, J=0.5, 7 Hz), 7.43 (t, 1H, J=6 Hz), 4.88 (m, 1H), 4.54 (m, 2H), 3.91 (s, 3H), 3.36 (m, 2H), 3.07 (s, 6H), 2.84 (s, 3H), 2.32 (m, 2H), 2.09 (m, 2H). IR (microscope) 2920, 1715, 1695, 1630, 1435, 1390, 1270, 1190 cm⁻¹. MS (DCI/NH₃) 489 (M+H)⁺. Anal calcd for $C_{26}H_{28}N_6O_4 \cdot HCl \cdot 3\ H_2O$: C, 53.93; H, 6.09; N, 14.51. Found: C, 54.09; H, 5.86; N, 13.92.

EXAMPLE 5

Preparation of 1-N,N-dimethylcarbamoyl-4-methoxycarbonyl-3-{[4-(1H-2-methylimidazo[4.5-c]pyrid-1-yl)methylpiperidin-1-yl]carbonyl}indole-1,4-dicarboxylic acid 1-dimethyl amide-4-methyl ester hydrochloride.

The desired compound was prepared according to the method of Example 1, except substituting indole-1,3,4-tricarboxylic acid 1-dimethyl amide 4-methyl ester (indole 3) for 6-(4-fluorophenyl)indole-1,3-dicarboxylic acid 1-dimethyl amide, and substituting 1H-1-(piperidin-4-ylmethyl)-2-methyl[4.5-c]imidazopyridine (amine 2) for 1H-1-(piperidin-4-yl)-2-methyl[4.5-c]imidazopyridine (amine 1). mp>200° C. (dec). ¹H NMR (DMSO-d6, 300 MHz) δ8.80 (s, 1H), 8.29 (d, 1H, J=6 Hz), 7.88 (s, 1H), 7.87 (dd, 1H, J=0.5, 6 Hz), 7.63 (m, 2H), 7.40 (t, 1H, J=6 Hz), 4.53 (m, 1H), 4.16 (d, 1H, J=7 Hz), 3.83 (m, 1H), 3.73 (s, 3H), 3.03 (s, 6H), 2.69 (m, 2H), 2.61 (s, 3H), 2.16 (m, 1H), 1.60 (m, 2H), 1.22 (m, 2H). IR (KBr) 3440, 2940, 2775, 1690, 1640, 1620, 1440, 1390 cm⁻¹. MS (DCI/NH₃) m/e 503 (M+H)⁺. Anal calcd for $C_{27}H_{30}N_6O_4 \cdot HCl \cdot 2.75\ H_2O$: C, 55.10; H, 6.25; N, 14.28. Found: C, 55.32; H, 6.72; N, 13.72.

EXAMPLE 6

Preparation of 6-(4-fluorophenyl)-3-{[4-(1H-2-methylimidazo[4.5-c]pyrid-1 -yl)methylpiperidin-1-yl]carbonyl}indole-1-carboxylic acid dimethyl amide hydrochloride.

The desired compound was prepared according to the method of Example 1, except substituting 1H-1-(piperidin-4-ylmethyl)-2-methyl[4.5-c]imidazopyridine (amine 2) for 1H-1-(piperidin-4-yl)-2-methyl[4.5-c]imidazopyridine (amine 1). ¹H NMR (DMSO-d6, 300 MHz) δ8.79 (s, 1H), 8.29 (d, 1H, J=6 Hz), 7.88 (s, 1H), 7.80 (d, 1H, J=1 Hz), 7.73 (m, 3H), 7.66 (dd, 1H, J=1,3 Hz), 7.52 (dd, 1H, J=2, 5 Hz), 7.31 (m, 2H), 4.18 (d, 2H, J=9 Hz), 3.83 (m, 2H), 3.03 (s, 6H), 2.69 (m, 2H), 2.61 (s, 3H), 2.16 (m, 1H), 1.60 (m, 2H), 1.22 (m, 2H). IR (microscope) 3400, 2930, 1685, 1615, 1515, 1475, 1440, 1385 cm⁻¹. MS (DCI/NH₃)m/e 539 (M+H)⁺, 231. Anal calcd for $C_{31}H_{31}FN_6O \cdot HCl \cdot 3.25\ H_2O$: C, 58.76; H, 6.12; N, 13.26. Found: C, 58.76; H, 6.28; N, 12.88.

EXAMPLE 7

Preparation of 4-chloro-3-{[4-(1H-2-methylimidazo[4.5-c]pyrid-1-yl)methylpiperidin-1-yl]carbonyl}indole-1-carboxylic acid dimethyl amide hydrochloride.

The desired compound was prepared according to the method of Example 1, except substituting 4-chloroindole-1,3-dicarboxylic acid 1-dimethyl amide (indole 4) for 6-(4-fluorophenyl)indole-1,3-dicarboxylic acid 1-dimethyl amide, and substituting 1H-1-(piperidin-4-ylmethyl)-2-methyl[4.5-c]imidazopyridine (amine 2) for ¹H-1 -(piperidin-4-yl)-2-methyl[4.5-c]imidazopyridine (amine 1). ¹H NMR (DMSO-d6, 300 MHz) δ8.78 (s, 1H), 8.27 (d, 1H, J=6 Hz), 7.79 (s, 1H), 7.58 (m, 2H), 7.27 (m, 2H), 4.14 (d, 2H, J=9 Hz), 3.53 (m, 2H), 3.03 (s, 6H), 2.67 (m, 2H), 2.63 (s, 3H), 2.16 (m, 1H), 1.40 (m, 2H), 0.99 (m, 2H). IR (KBr) 3440(br), 2930, 1695, 1630, 1390, 1180 cm⁻¹. MS (DCI/NH₃) m/e 479, 481 (M+H)⁺. Anal calcd for $C_{25}H_{27}ClN_6O_2 \cdot HCl$: C, 58.26; H, 5.48; N, 16.30. Found: C, 53.31; H, 7.22; N, 13.15.

EXAMPLE 8

Preparation of 1-(2-ethoxyethyl)-6-(4-fluorophenyl)-3-{[4-(1H-2-methylimidazo[4.5-c]1-yl]methylpiperidin-1-yl]carbonyl}indole hydrochloride.

Step 1: 6-(4-fluorophenyl)-3-{[4-(1H-2-methylimidazo[4.5-c]pyrid-1 -yl)methylpiperidin-1-yl]carbonyl}indole.

The desired compound was prepared according to the method of Example 1, except substituting 6-(4-fluorophenyl)indole-3-carboxylic acid (indole 2) for 6-(4-fluorophenyl)indole-1,3-dicarboxylic acid 1-dimethyl amide, and substituting 1H-1-piperidin-4-ylmethyl)-2-methyl[4.5-c]imidazopyridine (amine 2) for 1H-1-(piperidin-4-yl)-2- methyl[4.5-c]imidazopyridine (amine 1), and adding DMF to the reaction mixture.

Step 2: 1-(2-ethoxyethyl)-6-(4-fluorophenyl)-3-{[4-(1H-2-methylimidazo[4,5-c]pyrid-1-yl)methylpiperidin-1-yl]carbonyl}indole hydrochloride.

To a solution in DMF (6 mL) of 6-(4-fluorophenyl)-3-{[4-(1H-2-methylimidazo[4.5-c]pyrid-1-yl)piperidin-1-yl]carbonyl}indole (0.107 g, 0.23 mmol), prepared as in step 1, was added NaH (0.010 g, 0.40 mmol). After 5 minutes, a solution of 2-bromoethyl ethyl ether (0.042 g, 0.27 mmol) in DMF (2 mL) was added and the reaction mixture was stirred for 4 hours at ambient temperature. The reaction mixture was partitioned between ethyl acetate and brine. The organic phase was washed with brine, dried over $MgSO_4$, filtered, and concentrated in vacuo to give a brown liquid. The crude product was taken up in THF and treated with 4N HCl/dioxane (0.10 mL). The hydrochloride salt was isolated as an off-white powder by dilution with ether, filtration, and vacuum drying. $^1$H NMR (DMSO-d6, 300 MHz) δ9.35 (s, 1H), 8.64 (d, 1H, J=6 Hz), 8.38 (s, 1H), 7.84 (bds, 1H), 7.77 (m, 3H), 7.73 (dd, 1H, J=1,3 Hz), 7.42 (dd, 1H, J=2,5 Hz), 7.29 (m, 2H), 4.47 (d, 2H, J=9 Hz), 4.38 (m, 2H), 3.83 (m, 4H), 3.42 (q, 2H, J=7 Hz,) 2.89 (m, 2H), 2.77 (s, 3H), 2.22 (m, 1H), 1.55 (m, 2H), 1.40 (m, 2H), 1.02 (t, 3H, J=7 Hz). IR (KBr) 2920, 2850, 1655, 1635 $cm^{-1}$. Anal calcd for $C_{32}H_{34}N_5O_2F.2$ HCl.1.25 $H_2O$: C, 60.52; H, 6.11; N, 11.03. Found: C, 60.47; H, 6.01; N, 11.58.

EXAMPLE 9

Preparation of 1-(2-ethoxyethyl)-4-chloro-3-([4-(1H-2-methylimidazo[4.5-c]pyrid-1-yl)methylpiperidin-1-yl]carbonyl}indole hydrochloride.

Step 1: 4-chloro-3-{[4-(1H-2-methylimidazo[4.5-c]pyrid-1-yl)methylpiperidin-1-yl]carbonyl}indole.

To a solution in methanol (10 mL) of 4-chloro-3-{[4-(1H-2-methylimidazo[4.5-c]pyrid-1-yl)methylpiperidin-1-yl]carbonyl}indole-1-carboxylic acid dimethyl amide hydrochloride (0.292 g, 0.61 mmol), prepared as in Example 7, was added $K_2CO_3$ (1.0 g, 7.2 mmol) and the mixture was stirred at ambient temperature for 4 days. The reaction mixture was partitioned between $CH_2Cl_2$ and $H_2O$. The organic phase was dried over $MgSO_4$, filtered, and concentrated in vacuo to give 4-chloro-3-{[4-(1H-2-methylimidazo[4.5-c]pyrid-1-yl)methylpiperidin-1-yl]carbonyl}indole (0.224 g) as a yellow oil.

Step 2: 1-(2-ethoxyethyl)-4-chloro-3-{[4-(1H-2-methylimidazo[4.5-c]pyrid-1-yl)methylpiperidin-1-yl]carbonyl}indole hydrochloride.

The desired compound was prepared according to the method of Example 8, step 2, except substituting 4-chloro-3-{[4-(1H-2-methylimidazo[4.5-c]pyrid-1-yl)methylpiperidin-1-yl]carbonyl}indole, prepared as in step 1, for 6-(4-fluorophenyl)-3-{[4-(1H-2-methylimidazo[4.5-c]pyrid-1-yl)piperidin-1-yl]carbonyl}indole. 1H NMR (DMSO-d6, 300 MHz) δ9.36 (s, 1H), 8.62 (d, 2H, J=6 Hz), 8.31 (d, 1H, J=6 Hz), 7.56 (d, 1H, J=6 Hz), 7.50 (s, 1H), 7.16 (m, 2H), 4.38 (m, 4H), 3.70 (m, 2H), 3.38 (m,4H), 2.92 (m, 2H), 2.73 (s, 3H), 2.32 (m, 1H), 1.43 (m, 2H), 1.18 (m, 2H), 0.99 (t, 3H, J=7 Hz). IR (KBr) 3430 (br), 2940, 2860, 1625, 1440 $cm^{-1}$. MS ($DCI/NH_3$) 480, 482 (M+H)$^+$. Anal calcd for $C_{26}H_{30}ClN_5O_2.HCl.2.5$ $H_2O$: C, 55.62; H, 6.46; N, 12.47. Found: C, 55.64; H, 6.44; N, 12.18.

EXAMPLE 10

Preparation of 3-[{4-[(2-(1H-2-methylimidazo[4.5-c]pyrid-1-yl)ethyl]piperazin-1-yl}carbonyl]indole-1,4-dicarboxylic acid 1-dimethyl amide 4-methyl ester hydrochloride.

The desired compound was prepared according to the method of Example 1, except substituting indole-1,3,4-tricarboxylic acid 1-dimethyl amide 4-methyl ester (indole 3) for 6-(4-fluorophenyl)indole-1,3-dicarboxylic acid 1-dimethyl amide, and substituting 1H-1-[2-(piperazin-1-yl)ethyl]-2-methyl[4.5-c]imidazopyridine (amine 3) for 1H-1-(piperidin-4-yl)-2-methyl[4.5-c]imidazopyridine (amine 1). $^1$H NMR (DMSO-d6, 300 MHz) δ8.79 (s, 1H), 8.28 (d, 1H, J=6 Hz), 7.89 (s, 1H), 7.87 (d, 1H, J=6 Hz), 7.63 (d, 1H, J=7 Hz), 7.58 (d, 1H, J=7 Hz), 7.40 (t, 1H, J=7 Hz), 4.32 (m, 2H), 3.72 (s, 3H), 3.58 (m, 2H), 3.03 (s, 6H), 2.69 (m, 2H), 2.61 (s, 3H), 2.61 (m, 2H), 2.56 (m, 2H), 2.43 (m, 2H). IR (KBr) 3440, 2950, 1695, 1640, 1435, 1390 $cm^{-1}$. MS ($DCI/NH_3$) m/e 518 (M+H)$^+$, 246. Anal calcd for $C_{27}H_{31}N_7O_4.HCl.4$ $H_2O$: C, 51.80; H, 6.44; N, 15.66. Found: C, 51.98; H, 6.12; N, 15.21.

EXAMPLE 11

Preparation of 6-(4-fluorophenyl)-3-[{4-[(2-(1H-2-methylimidazo[4.5-c]pyrid-1-yl)ethyl]piperazin-1-yl}carbonyl]indole-1-carboxylic acid dimethyl amide hydrochloride.

The desired compound was prepared according to the method of Example 1, except substituting 1H-1-[2-(piperazin-4-yl)ethyl]-2-methyl[4.5-c]imidazopyridine (amine 3) for 1H-1-(piperidin4-yl)-2-methyl[4.5-c]imidazopyridine (amine 1). $^1$H NMR (DMSO-d6, 300 MHz) δ8.79 (s, 1H), 8.29 (d, 1H, J=6 Hz), 7.89 (s, 1H), 7.81 (bds, 1H), 7.73 (m, 3H), 7.59 (d, 1H, J=6 Hz), 7.52 (d, 1H, J=7 Hz), 7.30 (m, 2H), 4.32 (m, 2H), 3.58 (m, 2H), 3.03 (s, 6H), 2.69 (m, 2H), 2.61 (s, 3H), 2.61 (m, 2H), 2.56 (m, 2H), 2.43 (m, 2H). MS ($DCI/NH_3$) m/e 554 (M+H)$^+$.

EXAMPLE 12

Preparation of 6-(4-fluorophenyl)-3-{[4-(1H-2-methylimidazo[4.5-c]pyrid-1-yl)piperidin-1-yl]sulfonyl}indole-1-carboxylic acid t-butyl ester.

To a solution under $N_2$ of 1H-1-(piperidin-4-yl)-2-methyl[4.5-c]imidazopyridine (amine 1) (76 mg, 0.35 mmol) in THF (2 mL) was added triethylamine (70 μL, 0.50 mmol) and a solution of 1-tert-butoxycarbonyl-6-(4-fluorophenyl)indole- 3-sulfonyl chloride (Indole 5) (137 mg, 0.33 mmol) in THF (1.3 mL) and the reaction mixture was stirred for 48 hours at ambient temperature. The reaction mixture was filtered and the filtrate concentrated in vacuo and azeotroped with $CH_2Cl_2$ to give an orange foam (220 mg). Chromatography on silica gel (40:1, then 20:1 $CHCl_3$-methanol) gave 6-(4-fluorophenyl)-3-{[4-(1H-2-methylimidazo[4.5-c]pyrid-1-yl)piperidin-1-yl]sulfonyl}indole-1-carboxylic acid t-butyl ester (141 mg, 72%) as a yellow foam. $^1$H NMR (DMSO-d6, 300 MHz) δ1.69 (s, 9H), 1.89–1.99 (c, 2H), 2.30 (m, 2H), 2.51 (s, 3H), 2.78 (t, 2H, J=12 Hz), 4.01 (d, 2H, J=12 Hz), 4.44 (m, 1H), 7.32 (d, 1H, J=5.5 Hz), 7.36 (t, 2H, J(F-Hortho, Hortho-Hmeta)=8.8 Hz), 7.74 (dd, 1H, J=1.6, 8.3 Hz), 7.76 (dd, 2H, J(F-Hmeta, Hortho-Hmeta)= 5.5, 8.8 Hz), 8.00 (d, 1H, J=8.4 Hz), 8.11 (d, 1H, J=5.5 Hz), 8.25 (s, 1H), 8.44 (d, 1H, J=1.5 Hz), 8.75 (s, 1H). IR (microscope) 1068 (m), 1148 (s), 1232 (s), 1288 (m), 1362 (s), 1436 $cm^{-1}$. MS (FAB) m/e 628 (M+K)$^+$, 590 (M+H)$^+$. Anal calcd for $C_{31}H_{32}N_5O_4FS.0.4$ $H_2O$: C, 62.38; H, 5.54; N, 11.73. Found: C,.62.55; H, 5.70; N, 11.36.

EXAMPLE 13

Preparation of 6-(4-fluorophenyl)-3-{[4-(1H-2-methylimidazo[4.5-c]pyrid-1-yl)piperidin-1-yl]sulfonyl}indole.

The desired compound was prepared by treatment of a solution in THF of 6-(4-fluorophenyl)-3-{[4-(1H-2-methylimidazo[4.5-c]pyrid-1-yl)piperidin-1-yl]sulfonyl}indole-1-carboxylic acid t-butyl ester (124 mg, 0.21 mmol), prepared as in Example 12, with sodium methoxide (25% in methanol, 0.20 mL, 0.88 mmol). Pure 6-(4-fluorophenyl)-3-{[4-(1H-2-methylimidazo[4.5-c]pyrid-1-yl)piperidin-1-yl]sulfonyl}indole (51 mg, 50%) was obtained by recrystallization from ethyl acetate. mp 176°–180° C. $^1$H NMR (DMSO-d6, 300 MHz) δ1.82–1.94 (c, 2H), 2.24 (m, 2H), 2.51 (s, 3H), 2.68 (t, 2H, J=12 Hz), 3.97 (d, 2H, J=12 Hz), 4.40 (m, 1H), 7.16 (d, 1H, J=5.5 Hz), 7.32 (t, 2H, J(F-Hortho, Hortho-Hmeta)=8.8 Hz), 7.53 (dd, 1H, 1.5, 8.5 Hz), 7.74 (dd, 2H, J(F-Hmeta, Hortho-Hmeta)=5.3, 9.0 Hz), 7.79 (d, 1H, J=1.1 Hz), 7.92 (d, 1H, J=8.5 Hz), 8.08 (d, 1H, J=5.9 Hz), 8.10 (d, 1H, J=2.6 Hz), 8.74 (s, 1H), 12.33 (d, 1H, J=2.2 Hz). IR (microscope) 938 (m), 1124 (s), 1137 (s), 1297 (s), 1323 (m), 1362 (m), 1508 (m), 2928 (br), 3168 (br) cm$^{-1}$. MS (DCI/NH$_3$) m/e 490 (M+H)$^+$. Anal calcd for $C_{26}H_{24}N_5O_2FS.1.5\ H_2O$: C, 60.45; H, 5.26; N, 13.56. Found: C, 60.27; H, 5.19; N, 13.49.

EXAMPLE 14

Preparation of 6-(4-fluorophenyl)-3-{[4-(1H-2-methylimidazo[4.5-c]pyrid-1-yl)piperidin-1-yl]sulfonyl}indole-1-carboxylic acid dimethyl amide hydrochloride.

To a solution under N$_2$ of 6-(4-fluorophenyl)-3-{[4-(1H-2-methylimidazo[4.5-c]pyrid-1-yl)piperidin-1-yl]sulfonyl}indole (86 mg, 0.18 mmol), prepared as in Example 13, in THF (3.6 mL), was added powdered KOH (58 mg, (0.90 mmol), and the reaction mixture was stirred for 45 minutes at ambient temperature. Dimethylcarbamyl chloride (33 μL, 0.36 mmol) was added via syringe and the reaction mixture was stirred for 1 hour at ambient temperature. The reaction mixture was diluted with ethyl acetate and extracted twice with saturated aqueous NaHCO$_3$. The organic phase was dried over Na$_2$SO$_4$, filtered, and concentrated in vacuo to give a yellow foam (103 mg). Chromatography on silica gel (40:1, then 20:1 CHCl$_3$-methanol) gave 6-(4-fluorophenyl)-3-{[4-(1H-2-methylimidazo[4.5-c]pyrid-1-yl)piperidin-1-yl]sulfonyl}indole-1-carboxylic acid dimethyl amide (69 mg, 69%). The hydrochloride salt (52 mg, 71%) was prepared as described in Example 8, step 2. mp 135°–145° C. $^1$H NMR (DMSO-d6, 300 MHz) δ2.01–2.11 (c, 2H), 2.38 (m, 2H), 2.68 (s, 3H), 2.70 (t, 2H, J=11 Hz), 3.10 (s, 6H), 4.00 (d, 2H, J=11 Hz), 4.64 (m, 1H), 7.33 (t, 2H, J(F-Hortho, Hortho-Hmeta)=8.8 Hz), 7.66 (dd, 1H, J=1.5, 8.4 Hz), 7.76 (dd, 2H, J(F-Hmeta, Hortho-Hmeta)=5.5, 8.8 Hz), 7.90 (d, 1H, J=1.1 Hz), 7.99 (d, 1H, J=8.1 Hz), 8.22 (d, 1H, J=6.6 Hz), 8.35 (s, 1H), 8.50 (d, 1H, J=6.6 Hz), 9.32 (s, 1H). IR (microscope) 1155 (m), 1336 (m), 1355 (m), 1390 (s), 1477 (s), 1517 (s), 1700 (s), 2597 (br), 3401 (br) cm$^{-1}$. MS (DCI/NH$_3$) m/e 561 (M+H)$^+$ (free base). Anal calcd for $C_{29}H_{30}N_6O_3FSCl.\ 1.75\ H_2O$: C, 55.41; H, 5.37; N, 13.37. Found: C, 55.51; H, 5.41; N, 13.19.

EXAMPLE 15

Preparation of 6-(4-fluorophenyl)-3-{[4-(1H-2-methylimidazo[4.5-c]pyrid-1-yl)methylpiperidin-1-yl]sulfonyl)indole-1-carboxylic acid t-butyl ester.

To a suspension of 1H-1-(piperidin-4-ylmethyl)-2-methyl [4.5-c]imidazopyridine (amine 2) (69 mg, 0.30 mmol) in THF (1 mL) and dioxane (1 mL) was added triethylamine (0.60 mL, 0.43 mmol) and a solution of 1-tert-butoxycarbonyl-6-(4-fluorophenyl)indole-3-sulfonyl chloride (Indole 5) (110 mg, 0.27 mmol) in THF (1.6 mL) and the reaction mixture was stirred overnight at ambient temperature. The reaction mixture was diluted with CH$_2$Cl$_2$, concentrated in vacuo, and azeotroped with CH$_2$Cl$_2$. Chromatography on silica gel (80:1, then 40:1, then 20:1 CHCl$_3$-methanol) gave a peach foam which was chopped up and dried under vacuum to give 6-(4-fluorophenyl)-3-{[4-(1H-2-methylimidazo[4.5-c]pyrid-1-yl)methylpiperidin-1-yl]sulfonyl}indole-1-carboxylic acid t-butyl ester as a peach powder (100 mg, 62%). $^1$H NMR (DMSO-d6, 300 MHz) δ1.32–1.57 (c, 4H), 1.66 (s, 9H), 1.77–1.91 (c, 1H), 2.31 (t, 2H, J=11 Hz), 2.51 (s, 3H), 3.75 (d, 2H, J=12 Hz), 4.08 (d, 2H, J=7.4 Hz), 7.33 (t, 2H, J(F-Hortho, Hortho-Hmeta)=8.8 Hz), 7.54 (d, 1H, J=5.5 Hz), 7.65 (dd, 1H, J=1.5, 8.5 Hz), 7.72 (dd, 2H, J(F-Hmeta Hortho-Hmeta)=5.5, 8.8 Hz), 7.88 (d, 1H, J=8.1 Hz), 8.06 (s, 1H), 8.22 (d, 1H, J=5.5 Hz), 8.34 (d, 1H, J=1.5 Hz), 8.76 (s, 1H). IR (microscope) 819 (m), 1068 (m), 1146 (s), 1231 (s), 1286 (m), 1343 (s), 1367 (s), 1475 (m), 1518 (m), 1747 (s), 2935 (w), 2980 (w) cm$^{-1}$. MS (DCI/NH$_3$) m/e 604 (M+H)$^+$. Anal calcd for $C_{32}H_{34}N_5O_4FS.0.5\ H_2O.0.2\ Et_2O$: C, 61.42; H, 5.67; N, 11.12. Found: C, 61.43; H, 5.32; N, 11.00.

EXAMPLE 16

Preparation of 6-(4-fluorophenyl)-3-{[4-(1H-2-methylimidazo[4.5-c]pyrid-1-yl)methylpiperidin-1-yl]sulfonyl}indole.

The desired compound was prepared according to the method of Example 13, except substituting 6-(4-fluorophenyl)-3-{[4-(1H-2-methylimidazo[4.5-c]pyrid-1-yl)methylpiperidin-1-yl]sulfonyl}indole-1-carboxylic acid t-butyl ester (91 mg, 0.15 mmol), prepared as in Example 15, for 1-N,N-dimethylcarbamoyl-6-(4-fluorophenyl)-3-{4-[(1H-2-methylimidazo[4.5-c]pyrid-1-yl)piperidin-4-yl]sulfonyl}indole. Pure 6-(4-fluorophenyl)-3-{[4-(1H-2-methylimidazo[4.5c]pyrid-1-yl)methylpiperidin-1-yl]sulfonyl}indole (51 mg, 67%) was obtained by chromatography on silica gel (40:1, then 20:1, then 10:1 CHCl$_3$-methanol). $^1$H NMR (DMSO-d6, 300 MHz) δ1.32–1.55 (c, 4H), 1.71–1.86 (c, 1H), 2.14 (t, 2H, J=11.8 Hz), 2.51 (s, 3H), 3.70 (d, 2H, J=11.8 Hz), 4.06 (d, 2H, J=7.0 Hz), 7.29 (t, 2H, J(F-Hortho, Hortho-Hmeta)=8.8 Hz), 7.44 (dd, 1H, J=1.8, 8.5 Hz), 7.54 (dd, 1H, J=0.7, 5.5 Hz), 7.68 (d, 1H, J=1.1 Hz), 7.70 (dd, 2H, J(F-Hmeta, Hortho-Hmeta)=5.5, 8.8 Hz), 7.82 (d, 1H, J=8.5 Hz), 7.94 (s, 1H), 8.22 (d, 1H, J=5.5 Hz), 8.76 (s, 1H), 12.20 (d, 1H, J=2.9 Hz). IR (microscope) 736 (m), 811 (s), 1142 (s), 1156 (s), 1329 (s), 1399 (m), 1508 (m), 2855 (m), 2939 (m), 3090 (m) cm$^{-1}$. MS (DCI/NH$_3$) 503 (M+H)$^+$. Anal calcd for $C_{27}H_{26}N_5O_2FS.H_2O$: C, 62.17; H, 5.41; N, 13.43. Found: C, 62.15; H, 5.07; N, 13.23.

EXAMPLE 17

Preparation of 6-(4-fluorophenyl)-3-{[4-(1H-2-methylimidazo[4.5-c]pyrid-1-yl)methylpiperidin-1-yl]sulfonyl}indole-1-carboxylic acid dimethyl amide.

The desired compound was prepared according to the method of Example 14, except substituting 6-(4-fluorophenyl)-3-{[4-(1H-2-methylimidazo[4.5-c]pyrid-1-yl)methylpiperidin-1-yl]sulfonyl}indole (41 mg, 0.81 mmol), prepared as in Example 16, for 6-(4-fluorophenyl)-3-{[4-(1H-2-methylimidazo[4.5-c]pyrid-1-yl]sulfonyl}indole. Chromatography on silica gel (40:1, then 20:1 CHCl$_3$-methanol) gave 6-(4-fluorophenyl)-3-{[4-(1H-2-methylimidazo[4.5-c]pyrid-1-yl)methylpiperidin-1-yl]sulfonyl}indole-1-carboxylic acid dimethyl amide as a whim foam, which was chopped up and dried under vacuum to give the free base (34 mg, 74%) as a white powder. $^1$H NMR (DMSO-d6, 300 MHz) δ1.33–1.57 (c, 4H), 1.76–1.92 (c, 1H), 2.27 (t, 2H, J=11.8 Hz), 2.51 (s, 3H), 3.04 (s, 6H), 3.74 (d, 2H, J=11.4 Hz), 4.06 (d, 2H, J=7.4 Hz), 7.30 (t, 2H, J(F-Hortho, Hortho-Hmeta) =9.0 Hz), 7.54 (d, 1H, J=5.5 Hz), 7.58 (dd, 1H, J=1.6, 8.2 Hz), 7.72 (dd, 2H, J(F-Hmeta, Hortho-Hmeta)=5.5, 8.8 Hz), 7.82 (d, 1H, J=1.1 Hz), 7.88 (d, 1H, J=8.5 Hz), 8.18 (s, 1H), 8.22 (d, 1H, J=5.5 Hz), 8.75 (s, 1H). IR (microscope) 821 (m), 1159 (s), 1338 (m), 1353 (m), 1392 (s), 1476 cm$^{-1}$. MS (DCI/NH$_3$) m/e 575 (M+H)$^+$. Anal calcd for $C_{30}H_{31}N_6O_3FS.0.6 H_2O.0.3 Et_2O$: C., 61.66; H, 5.84; N, 13.83. Found: C, 61.72; H, 5.52; N, 13.65.

EXAMPLE 18

Preparation of 6-(4-fluorophenyl)-3-[{4-[(2-(1H-2-methylimidazo[4.5-c]pyrid-1-yl)ethyl]piperazin-1-yl}sulfonyl] indole-1-carboxylic acid dimethyl amide.

Step 1: 6-(4-fluorophenyl)-3-[{4-[(2-(1H-2-methylimidazo[4.5-c]pyrid-1 -yl)ethyl]piperazin-1-yl}sulfonyl]indole-1-carboxylic acid t-butyl ester.

The desired compound was prepared according to the method of Example 15, except substituting 1H-1-[2-(piperazin-1-yl)ethyl]-2-methyl[4.5-c]imidazopyridine (amine 3) for 1H-1-(piperidin-4-ylmethyl)-2-methyl[4.5-c]imidazopyridine (amine 2).

Step 2: 6(4-fluorophenyl)-3-[{4-[(2-(1H-2-methylimidazo[4.5-c]pyrid-1-yl)ethyl]piperazin-1-yl}sulfonyl]indole.

The desired compound was prepared according to the method of Example 16, except substituting 6-(4-fluorophenyl)-3-[{4-[(2-(1H-2-methylimidazo[4.5-c]pyrid-  1-yl)ethyl]piperazin-1-yl}sulfonyl]indole-1-carboxylic acid t-butyl ester, prepared as in step 1, for 6-(4-fluorophenyl)-3-{[4-(1H-2-methylimidazo[4.5-c]pyrid-1 -yl)methylpiperidin-1-yl]sulfonyl}indole.

Step 3: 6-(4-fluorophenyl)-3-[{4-[(2-(1H-2-methylimidazo[4.5-c]pyrid-1yl)ethyl]piperazin-1-yl}sulfonyl]indole-1-carboxylic acid dimethyl amide.

The desired compound was prepared according to the method of Example 17, except substituting 6-(4-fluorophenyl)-3-[{4-[(2-(1H-2-methylimidazo[4.5-c]pyrid-1-yl) ethyl]piperazin-1-yl}sulfonyl]indole, prepared as in step 2, for 6-(4-fluorophenyl)-3-{[4-(1H-2-methylimidazo[4.5-c]pyrid-1-yl)methylpiperidin-1-yl]sulfonyl}indole. mp95°–105° C. $^1$H NMR(DMSO-d6, 300 MHz) δ2.47 (s, 3H), 2.54(br, 4H), 2.62 (t, 2H, J=6.2 Hz), 2.93 (br, 4H), 3.05 (s, 6H), 4.22 (t, 2H, J=6.2 Hz), 7.32 (t, 2H, J(F-Hortho, Hortho-Hmeta)=8.8 Hz), 7.44 (d, 1H, J=5.5 Hz), 7.62 (dd, 1H, J=1.4, 8.2 Hz), 7.76 (dd, 2H, J(F-Hmeta, Hortho-Hmeta)=5.5, 8.5 Hz), 7.84 (s, 1H), 7.89 (d, 1H, J=8.5 Hz), 8.08 (d, 1H, J=5.2 Hz), 8.23 (s, 1H), 8.71 (s, 1H). IR (microscope) 1161 (s), 1352 (m), 1391 (s), 1476 (m), 1516 (m), 1702 (s), 2852 (br w), 2934 (br w) cm$^{-1}$. MS (DCI/NH$_3$) m/e 590 (M+H)$^+$. Anal calcd for $C_{30}H_{32}N_7O_3SF.0.65 H_2O.0.3 Et_2O$: C, 60.09; H, 5.87; N, 15.72. Found: C, 60.07; H, 5.90; N, 15.72.

EXAMPLE 19

Preparation of 6-(4-fluorophenyl)-3-{[4-(1H-2-methylimidazo[4.5-c]pyrid-1 -yl)piperidin-1-yl]acetyl}indole.

To a solution under N$_2$ of 1H-1-(piperidin-4-yl)-2-methyl [4.5-c]imidazopyridine (amine 1) (100 mg, 0.462 mmol) in DMF (1 mL) was added N,N-diisopropylethylamine (0.16 mL, 0.92 mmol) and a solution of 6-(4-fluorophenyl)-3-chloroacetylindole (indole 6) (127 mg, 0.441 mmol) in THF (2 mL) and DMF (2 mL) over 105 minutes. The reaction mixture was stirred overnight at ambient temperature and then was diluted with ethyl acetate and extracted twice with aqueous 0.1M NaOH. The organic phase was dried over Na$_2$SO$_4$, filtered, and concentrated in vacuo to give an orange foam (0.18 g). Chromatography on silica gel (50:1 CHCl$_3$-methanol +0.5% NH$_4$OH, then 20:1 CHCl$_3$-methanol+0.5% NH$_4$OH, then 10:1 CHCl$_3$-methanol+0.5% NH$_4$OH gave 6-(4-fluorophenyl)-3-{[4-(1H-2-methylimidazo[4.5-c]pyrid-1-yl)piperidin-1-yl]acetyl}indole (46 mg, 22%) as a light-orange powder. $^1$H NMR (DMSO-d6, 300 MHz) δ1.84–1.94 (c, 2H), 2.32–2.48 (c, 4H), 2.63 (s, 3H), 3.11–3.20 (c, 2H), 3.74 (s, 2H), 4.30–4.43 (c, 1H), 7.29 (t, 2H, J(F-Hortho, Hortho-Hmeta)=9.0 Hz), 7.49 (dd, 1H, J=1.5, 8.5 Hz), 7.64 (dd, 1H, J=0.7, 5.9 Hz), 7.70 (d, 1H, J=1.1 Hz), 7.73 (dd, 2H, J(F-Hmeta, Hortho-Hmeta)=5.4, 9.0 Hz), 8.24 (d, 1H, J=6.6 Hz), 8.26 (d, 1H, J=8.5 Hz), 8.62 (d, 1H, J=2.9 Hz), 8.80 (s, 1H), 12.02 (br s, 1H). MS (DCI/NH$_3$) m/e 468 (M+H)$^+$. Anal calcd for $C_{28}H_{26}N_5O_5F.H_2O$: C, 69.26; H, 5.81; N, 14.42. Found: C, 69.18; H, 5.60; N, 14.31.

EXAMPLE 20

Preparation of 6-(4-fluorophenyl)-3-{4-(1H-2-methylimidazo[4.5c]pyrid-1 -yl)piperidin-1-yl]acetyl}indole-1-carboxylic acid dimethyl amide.

The desired compound was prepared according to the method of Example 14, except substituting 6 (4-fluorophenyl)-3-{[4-(1H-2-methylimidazo[4.5-c]pyrid-1 -yl)piperidin-1-yl]acetyl}indole, prepared as in Example 19, for 6-(4-fluorophenyl)-3-{[4-(1H-2-methylimidazo[4.5-c]pyrid-1-yl)piperidin-1-yl]sulfonyl}indole, and dissolving the indole in 2:1 THF-DMF. $^1$H NMR (DMSO-d6, 300 MHz) δ1.85–1.94 (c, 2H), 2.32–2.48 (c, 4H), 2.63 (s, 3H), 3.10–3.19 (c, 2H), 3.14 (s, 6H), 3.79 (s, 2H), 4.31–4.45 (c, 1H), 7.31 (t, 2H, J(F-Hortho, Hortho-Hmeta)=8.8 Hz), 7.62 (dd, 1H, J=1.6, 8.2 Hz), 7.63 (dd, 1H, J=0.7, 4.8 Hz), 7.75 (dd, 2H, J(F-Hmeta, Hortho-Hmeta)=5.2, 8.8 Hz), 7.82 (d, 1H, J=1.1 Hz), 8.25 (d, 1H, J=5.5 Hz), 8.32 (d, 1H, J=8.1 Hz), 8.80 (s, 1H), 8.89 (s, 1H). IR (microscope) 812 (s), 1389 (s), 1481 (m), 1516 (m), 1606 (w), 1658 (w), 1699 (s), 2810 (br), 293 1 (br) cm$^{-1}$. MS (DCI/NH$_3$) 539 (M+H)$^+$. Anal calcd for $C_{31}H_{31}N_6O_2.F\ 0.8\ H_2O.1.5\ Et_2O$: C, 67.26; H, 6.14; N, 14.80. Found: C, 67.27; H, 5.79; N, 14.61.

EXAMPLE 21

Preparation of 3-{[4-(1H-2-methylimidazo[4.5-c]pyrid-1-yl)piperidin-1-yl]acetyl}indole-4-carboxylic acid methy ester.

The desired compound was prepared according to the method of Example 19, except substituting 4-methoxycarbonyl-3-chloroacetylindole (Indole 7), for 6-(4-fluorophenyl)-3-chloroacetylindole, and using DMF instead of 2:1 THF-DMF. mp 186°–187° C. $^1$H NMR (DMSO-d6, 300 MHz) δ1.85 (d, 2H, J=12 Hz), 2.28 (q, 2H, J=12 Hz), 2.41 (t, 2H, J=11 Hz), 2.61 (s, 3H), 3.07 (d, 2H, J=11 Hz), 3.67 (s, 2H), 3.79 (s, 3H), 4.32 (m, 1H), 7.29 (t, 1H, J=7.6 Hz), 7.34 (dd, 1H, J=1.5, 7.4 Hz), 7.57 (dd, 1H, J=0.9, 5.7 Hz), 7.66 (dd, 1H, J=1.6, 7.6 Hz), 8.24 (d, 1H, J=5.5 Hz), 8.53 (d, 1H, J=2.6 Hz), 8.79 (s, 1H), 12.16 (br s, 1H). IR (microscope) 1113 (m), 1126 (m), 1294 (m), 1350 (m), 1421 (m), 1436(m), 1510(m), 1612(m), 1653 (s), 1692(s),2950(m), 3111 (m), 3354 (br) cm$^{-1}$. MS (DCI/NH$_3$) m/e 432 (M+H)$^+$. Anal calcd for $C_{24}H_{25}N_5O_3.H_2O$: C, 64.13; H, 6.05; N, 15.58. Found: C, 64.06; H, 6.00; N, 15.44.

EXAMPLE 22

Preparation of 3-{[4-(1H-2-methylimidazo[4.5-c]pyrid-1-yl)piperidin-1-yl]acetyl}indole-1,4-dicarboxylic acid 1-dimethyl amide 4-methyl ester.

The desired compound was prepared according to the method of Example 20, except substituting 3-{[4-(1H-2-methylimidazo[4.5-c]pyrid-1-yl)piperidin-1-yl]acetyl}indole-4-carboxylic acid methy ester, prepared as in Example 21, for 6-(4-fluorophenyl)-3-{[4-(1H-2-methylimidazo[4.5-c]pyrid-1-yl)piperidin-1-yl]acetyl}indole. mp 93°–100° C. $^1$H NMR (DMSO-d6, 300 MHz) δ1.84 (d, 2H, J=12 Hz), 2.24 (q, 2H, J=12 Hz), 2.41 (t, 2H, J=11 Hz), 2.61 (s, 3H), 3.07 (d, 2H, J=12 Hz), 3.12 (s, 6H), 3.69 (s, 2H), 3.80 (s, 3H), 4.33 (m, 1H), 7.45 (t, 1H, J=7.8 Hz), 7.50 (dd, 1H, J=0.9, 5.7 Hz), 7.51 (dd, 1H, J=1.5, 7.4 Hz), 7.82 (dd, 1H, J=1.3, 7.9 Hz), 8.24 (d, 1H, J=5.9 Hz), 8.73 (s, 1H), 8.78 (d, 1H, J=0.7 Hz). IR (microscope) 1111 (m), 1188 (m), 1286 (m), 1358 (m), 1390 (s), 1431 (m), 1606 (w), 1699 (s), 1724 (s), 2948 (w) cm$^{-1}$. MS (DCI/NH$_3$) m/e 503 (M+H)$^+$. Anal calcd for $C_{27}H_{30}N_6O_4 \cdot H_2O$: C, 62.29; H, 6.20; N, 16.14. Found: C, 62.44; H, 5.90; N, 16.04.

EXAMPLE 23

Preparation of 1-(2-ethoxyethyl)-3-{[4-(1H-2-methylimidazo[4.5-c]pyrid-1 -yl)piperidin-1-yl]acetyl}indole-1-carboxylic acid methyl ester.

To a suspension under N$_2$ of 3-{[4-(1H-2-methylimidazo [4.5-c]pyrid-1-yl)piperidin-1-yl]acetyl}indole-4-carboxylic acid methy ester (1.00 g, 2.32 mmol), prepared as in Example 21, in DMF, was added NaH (95%, 71 mg, 2.8 mmol). After stirring for 20 minutes, N,N-diisopropylethylamine (1.2 mL, 6.9 mmol) was added, and a solution of 2-bromoethyl ethyl ether (0.44 mL, 3.5 mmol) in DMF (4 mL) was added dropwise. The reaction mixture was stirred for 27 hours at ambient temperature and then was diluted with ethy acetate and washed twice with 0.1M aqueous NaOH. The aqueous phase was taken to pH 12 with 1M aqueous NaOH and extracted with ethyl acetate. The process was repeated and the combined organic layers were dried over Na$_2$SO$_4$, filtered, and concentrated in vacuo to give a clear-orange oil (0.36 g). Chromatography on silica gel (40:1 CHCl$_3$-methanol+0.5% NH$_4$OH, then 20:1 CHCl$_3$-methanol+0.5% NH$_4$OH) gave 1-(2-ethoxyethyl)-3-{[4--(1H-2-methylimidazo[4.5-c]pyrid-1-yl)piperidin-1-yl] acetyl}indole-1-carboxylic acid methyl ester (1.01 g, 86%) as a pale-yellow powder. $^1$H NMR (DMSO-d6, 300 MHz) δ1.00 (t, 3H, J=7.0 Hz), 1.84 (d, 2H, J=11 Hz), 2.29 (q, 2H, J=11 Hz), 2.39 (t, 2H, J=11 Hz), 2.61 (s, 3H), 3.05 (d, 2H, J=10 Hz), 3.40 (q, 2H, J=7.0 Hz), 3.62 (s, 2H), 3.78 (t, 2H, J=5 Hz), 3.79 (s, 3H), 4.33 (m, 1H), 4.51 (t, 2H, J=5.2 Hz), 7.31–7.40 (c, 2H), 7.58 (dd, 1H, J=0.8, 5.6 Hz), 7.82 (dd, 1H, J=2.1, 7.0 Hz), 8.24 (d, 1H, J=5.5 Hz), 8.60 (s, 1H), 8.79 (s, 1H). IR (microscope) 1114 (s), 1198 (m), 1286 (s), 1360 (m), 1394 (s), 1435 (s), 1524 (s), 1607 (s), 1651 (m), 1723 (s), 2949 (m), 3394 (br) cm$^{-1}$. MS (DCI/NH$_3$) m/e 504 (M+H)$^+$. Anal calcd for $C_{28}H_{33}N_5O_4 \cdot 1.5 H_2O$: C, 63.38; H, 6.84; N, 13.20. Found: C, 63.64; H, 6.42; N, 12.79.

EXAMPLE 24

Preparation of 4-chloro-3-{[4-(1H-2-methylimidazo[4.5-c] pyrid-1-yl)piperidin-1-yl]acetyl}indole.

The desired compound was prepared according to the method of Example 19, except substituting 4-chloro-3-chloroacetylindole (indole 8) for 6-(4-fluorophenyl)-3-chloroacetylindole. $^1$H NMR (DMSO-d6, 300 MHz) δ1.87 (d, 2H, J=12 Hz), 2.30 (q, 2H, J=13 Hz), 2.46 (t, 2H, J=12 Hz), 2.63 (s, 3H), 3.12 (d, 2H, J=12 Hz), 3.77 (s, 2H), 4.34 (m, 1H), 7.20 (d, 1H, J=2.9 Hz), 7.21 (d, 1H, J=5.9 Hz), 7.48 (dd, 1H, J=3.1, 6.0 Hz), 7.56 (dd, 1H, J=0.9, 5.7 Hz), 8.22 (d, 1H, J=5.5 Hz), 8.48 (s, 1H), 8.79 (d, 1H, J=0.7 Hz), 12.16 (br s, 1H). IR (microscope) 740 (m), 1109 (s), 1291 (m), 1308 (m), 1360 (m), 1388 (m), 1414 (s), 1434(m), 1451 (m), 1468(m), 1520(m), 1610(m), 1661 (s), 2813 (m), 2931 (m), 3154 (br) cm$^{-1}$. MS (DCI/NH$_3$) m/e 408, 410 (M+H)$^+$. Anal calcd for $C_{22}H_{22}N_5OCl \cdot 1.75 H_2O$: C, 60.13; H, 5.84; N, 15.93. Found: C, 60.36; H, 5.48; N, 15.56.

EXAMPLE 25

Preparation of 1-(2-ethoxyethyl)-4-chloro-3-{[4-(1H-2-methylimidazo4.5-c]pyrid-1-yl)piperidin-1-yl]acetyl}indole.

The desired compound was prepared according to the method of Example 23, except substituting 4-chloro-3-{[4-(1H-2-methylimidazo[4.5-c]pyrid-1-yl)piperidin-1-yl] acetyl}indole, prepared as in Example 24, for 3-{[4-(1H-2-methylimidazo[4.5c]pyrid-1-yl)piperidin-1-yl] acetyl}indole-4-carboxylic acid methy ester. mp 59°–65° C. $^1$H NMR (DMSO-d6, 300 MHz) δ1.01 (t, 3H, J=7.0 Hz), 1.86 (d, 2H, J=12 Hz), 2.30 (q, 2H, J=12 Hz), 2.44 (t, 2H, J=11 Hz), 2.62 (s, 3H), 3.10 (d, 2H, J=11 Hz), 3.40 (q, 2H, J=7.0 Hz), 3.74 (s, 2H), 3.76 (t, 2H, J=5.4 Hz), 4.34 (m, 1H), 4.46 (t, 2H, J=5.4 Hz), 7.24 (d, 1H, J=1.8 Hz), 7.26 (d, 1H, J=7.4 Hz), 7.54 (d, 1H, J=5.5 Hz), 7.62 (dd, 1H, J=2.0, 7.2 Hz), 8.22 (d, 1H, J=5.9 Hz), 8.50 (s, 1H), 8.79 (s, 1H). IR (microscope) 1089 (m), 1115 (s), 1290 (m), 1359 (s), 1394 (s), 1435 (s), 1468 (m), 1523 (s), 1607 (m), 1659 (s), 2808 (w), 2866 (w), 2934 (w), 2972 (w), 3392 (br) cm$^{-1}$. MS (DCI/NH$_3$) m/e 480 (M+H)$^+$. Anal calcd for $C_{26}H_{30}N_5O_2Cl \cdot 0.75 H_2O$: C, 63.28; H, 6.43; N, 14.19. Found: C, 63.32; H, 6.61; N, 14.18.

EXAMPLE 26

Preparation of 4-chloro-3-{[4-(1H-2-methylimidazo[4.5-c] pyrid-1-yl)piperidin-1-yl]acetyl}indole-1-carboxylic acid dimethyl amide.

The desired compound was prepared according to the method of Example 20, except substituting 4-chloro-3-{[4-(1H-2-methylimidazo[4.5-c]pyrid-1-yl)piperidin-1-yl] acetyl}indole, prepared as in Example 24, for 6-(4-fluorophenyl)-3-{[4-(1H-2 -methylimidazo[4.5-c]pyrid-1-yl)piperidin-1-yl]acetyl}indole. mp 79°–83° C. $^1$H NMR (DMSO-d6, 300 MHz) δ1.86 (d, 2H, J=12 Hz), 2.26 (q, 2H, J=12 Hz), 2.45 (t, 2H, J=11 Hz), 2.61 (s, 3H), 3.09 (s, 6H), 3.11 (d, 2H, J=11 Hz), 3.80 (s, 2H), 4.34 (m, 1H), 7.35 (d, 1H, J=2.6 Hz), 7.36 (d, 1H, J=6.6 Hz), 7.47 (dd, 1H, J=1.1, 5.5 Hz), 7.62 (dd, 1H, J=2.8, 6.4 Hz), 8.22 (d, 1H, J=5.9 Hz), 8.63 (s, 1H), 8.78 (d, 1H, J=0.7 Hz). IR (microscope) 1106 (m), 1184 (m), 1359 (m), 1390 (s), 1426 (m), 1468 (m), 1524 (w), 1607 (w), 1700 (s), 2935 (w), 3392 (br) cm$^{-1}$. MS (DCI/NH$_3$) m/e 479 (M+H)$^+$. Anal calcd for $C_{35}H_{27}N_6O_2Cl \cdot 0.5 H_2O$: C, 61.53; H, 5.78; N, 17.22. Found: C, 61.32; H, 5.79; N, 16.87.

EXAMPLE 27

Preparation of 4-methyl-3-{[4-(1H-2-methylimidazo[4.5-c] pyrid-1-yl)piperidin-1-yl]acetyl}indole.

The desired compound was prepared according to the method of Example 19, except substituting 4-methyl-3-chloroacetylindole (indole 9) for 6-(4-fluorophenyl)-3-chloroacetylindole, and adding the solution of indole in DMF to the reaction mixture over 5 minutes. mp 118°–128° C. $^1$H NMR (DMSO-d6, 300 MHz) δ1.88 (d, 2H, J=11 Hz), 2.34 (q, 2H, J=11 Hz), 2.46 (t, 2H, J=11 Hz), 2.63 (s, 3H), 2.71 (s, 3H), 3.14 (d, 2H, J=11 Hz), 3.77 (s, 2H), 4.35 (m, 1H), 6.92 (d, 1H, J=7.0 Hz), 7.10 (t, 1H, J=7.8 Hz), 7.30 (d, 1H, J=8.1 Hz), 7.62 (dd, 1H, J=0.7, 5.5 Hz), 8.23 (d, 1H, J=5.5 Hz), 8.48 (s, 1H), 8.79 (s, 1H), 11.89 (br s, 1H). IR (microscope) 1113 (m), 1362 (m), 1402 (s), 1436 (m), 1520 (m), 1610 (m), 1651 (s), 2808 (br), 2950 (br), 3271 (br) cm$^{-1}$. MS (DCI/NH$_3$) m/e 388 (M+H)$^+$. Anal calcd for $C_{23}H_{25}N_5O \cdot H_2O \cdot 0.2\ CH_2Cl_2$: C, 65.96; H, 6.54; N, 16.58. Found: C, 65.95; H, 6.39; N, 16.48.

EXAMPLE 28

Preparation of 1-(2-ethoxyethyl)-4-methyl-3-{[4-(1H-2-methylimidazo[4.5-c]pyrid-1-yl)piperidin-1-yl]acetyl}indole.

The desired compound was prepared according to the method of Example 23, except substituting 4-methyl-3-{[4-(1H-2-methylimidazo[4.5-c]pyrid-1-yl)piperidin-1-yl] acetyl}indole, prepared as in Example 27, for 3-{[4-(1H-2-methylimidazo[4.5-c]pyrid-1-yl)piperidin-1-yl] acetyl}indole-4-carboxylic acid methy ester. $^1$H NMR (DMSO-d6, 300 MHz) δ1.04 (t, 3H, J=7.0 Hz), 1.89 (d, 2H, J=11 Hz), 2.36 (q, 2H, J=11 Hz), 2.45 (t, 2H, J=11 Hz), 2.63 (s, 3H), 2.71 (s, 3H), 3.14 (d, 2H, J=10 Hz), 3.42 (q, 2H, J=7.0 Hz), 3.74 (s, 2H), 3.77 (t, 2H, J=5.5 Hz), 4.36 (m, 1H), 4.43 (t, 2H, J=5.3 Hz), 6.97 (d, 1H, J=7.0 Hz), 7.15 (t, 1H, J=7.8 Hz), 7.42 (d, 1H, J=8.1 Hz), 7.63 (dd, 1H, J=1.0, 5.7 Hz), 8.23 (d, 1H, J=5.5 Hz), 8.53 (s, 1H), 8.79 (s, 1H). IR (microscope) 1112 (s), 1288 (m), 1358 (s), 1390 (s), 1432 (m), 1465 (m), 1523 (s), 1606 (m), 1649 (s), 2807 (w), 2865 (w), 2929 (w) cm$^{-1}$. MS (FAB) m/e 460 (m+1)$^+$. Anal calcd for $C_{27}H_{33}N_5O_2 \cdot 0.5\ H_2O$: C, 69.20; H, 7.31; N, 14.94. Found: C, 69.39; H, 7.10; N, 14.82.

EXAMPLE 29

Preparation of 4-methyl-3-{[4-(1H-2-methylimidazo[4.5:c]pyrid-1-yl)piperidin-1-yl]acetyl}indole-1-carboxylic acid dimethyl amide.

The desired compound was prepared according to the method of Example 20, except substituting 4-methyl-3-{[4-(1H-2-methylimidazo[4.5-c]pyrid-1-yl)piperidin-1-yl] acetyl}indole, prepared as in Example 27, for 6-(4-fluorophenyl)-3-{[4-(1H-2-methylimidazo[4.5-c]pyrid-1-yl)piperidin-1-yl]acetyl}indole, and dissolving the indole staging material in THF/DMF. $^1$H NMR (DMSO-d6, 300 MHz) δ1.88 (d, 2H, J=12 Hz), 2.32 (q, 2H, J=12 Hz), 2.46 (t, 2H, J=11 Hz), 2.63 (s, 3H), 2.66 (s, 3H), 3.09 (s, 6H), 3.14 (d, 2H, J=11 Hz), 3.81 (s, 2H), 4.36 (m, 1H), 7.06 (d, 1H, J=7.4 Hz), 7.24 (t, 1H, J=7.8 Hz), 7.44 (d, 1H, J=8.1 Hz), 7.58 (dd, 1H, J=1.0, 5.8 Hz), 8.23 (d, 1H, J=5.8 Hz), 8.69 (s, 1H), 8.79 (s, 1H). IR (microscope) 721 (m), 1134 (s), 1186 (s), 1200 (s), 1433 (m), 1553 (s), 1616 (s), 1675 (s), 2760 (m), 2866 (m), 2988 (m) cm$^{-1}$. MS (FAB) m/e 459 (M+1)$^+$. Anal calcd for $C_{26}H_{30}N_6O_2 \cdot H_2O$: C, 65.53; H, 6.77; N, 17.63. Found: C, 65.46; H, 6.62; N, 17.89.

EXAMPLE 30

Preparation of 3-{[trans-4-[(1H-2-methylimidazo[4.5-c]pyrid-1-yl)methylcyclohex-1-yl]carbonyl}indole-1,4-dicarboxylic acid 1-dimethyl amide 4-methyl ester hydrochloride.

Step 1: trans-4-(N-carbobenzyloxy)aminomethyl-1-cyclohexane carboxylic acid.

To a 0° C. solution of trans-4-aminomethyl-1-cyclohexane carboxylic acid (6.28 g, 0.04 mol) in 10% aqueous NaOH (16 mL) was added dropwise benzyl chloroformate (8.29 g, 0.049 mol) and 10% aqueous NaOH (20 mL). The cold bath was removed and the reaction mixture was stirred vigorously for one hour. The thick white paste was shaken with aqueous 1M HCl (100 mL) and the white solid was isolated by filtration, washed with H$_2$O, and dried overnight in vacuo to give trans-4-(N-carbobenzyloxy)aminomethyl-1-cyclohexane carboxylic acid.

Step 2: trans-4-(N-carbobenzyloxy)aminomethyl-1-cyclohexane carbonyl chloride.

A mixture of trans-4-(N-carbobenzyloxy)aminomethyl-1-cyclohexane carboxylic acid (5.02 g, 17.3 mmol), prepared as in step 1, and thionyl chloride was heated at 40° C. for 30 minutes. The reaction mixture was cooled to ambient temperature and diluted with pentane (50 mL). Trans-4-(N-carbobenzyloxy)aminomethyl-1-cyclohexane carbonyl chloride (4.37 g) was isolated by filtration and drying in vacuo.

Step 3: 3-[(trans-1-(N-carbobenzyloxy)aminomethylcyclohex-4-yl)carbonyl]indole-4-carboxylic acid methyl ester.

To a solution of indole-4-carboxylic acid methyl ester (2.33 g, 13.3 mmol) in CH$_2$Cl$_2$ (25 mL) was added ethylmagnesium bromide (3M in ether, 4.4 mL, 13.2 mmol). The reaction mixture was stirred for five minutes and ZnCl$_2$ (1M in ether, 40 mL, 40 mmol) was added and the cloudy, brown suspension was stirred for 15 minutes. A solution of trans-4-(N-carbobenzyloxy)aminomethyl-1-cyclohexane carbonyl chloride (4.36 g, 14.1 mmol), prepared as in step 2, in CH$_2$Cl$_2$ (20 mL) was added and the reaction mixture was stirred for three hours. The reaction mixture was poured into a separatory funnel containing saturated aqueous NH$_4$Cl which left a green-brown gum. The gum was broken up by trituration with aqueous 1M HCl and CH$_2$Cl$_2$/methanol and added to the separatory funnel. The layers were separated and the organic phase was washed with saturated aqueous NaHCO$_3$, dried over MgSO$_4$, filtered, and concentrated in vacuo. Chromatography on silica gel (1%, then 3% methanol/CH$_2$Cl$_2$) gave 3-[(trans-4-(N-carbobenzyloxy)aminomethylcyclohex-1-yl)carbonyl]indole-4-carboxylic acid methyl ester (2.83 g, 48%) as a tan foam.

Step 4: 3-[(trans-1-(N-carbobenzyloxy)aminomethylcyclohex-4-yl)carbonyl]indole-1,4-dicarboxylic acid 1-dimethyl amide 4-methyl ester.

The desired compound was prepared by treatment of a solution in THF of 3-[(trans-4-(N-carbobenzyloxy)aminomethylcyclohex-1-yl)carbonyl]indole-4-carboxylic acid methyl ester, prepared as in step 3, with KOH and dimethylcarbamyl chloride as described in Example 14.

Step 5: 3-[(trans-1-aminomethylcyclohex-4-yl)carbonyl]indole-1,4-dicarboxylic acid 1-dimethyl amide 4-methyl ester.

The desired compound was prepared by catalytic hydrogenation (10% Pd/C, 4 atm H$_2$, ethanol, 17 hours) of 3-[(trans-1-(N-carbobenzyloxy)aminomethylcyclohex-4-yl)carbonyl]indole-1,4-dicarboxylic acid 1-dimethyl amide 4-methyl ester.

Step 6: 3-[(trans-1-(N-3-nitropyrid-3-yl)aminomethylcyclohex-4-yl)carbonyl]indole-1,4-dicarboxylic acid 1-dimethyl amide 4-methyl ester.

A mixture of 3-[(trans-1-aminomethylcyclohex-4-yl)carbonyl]indole-1,4-dicarboxylic acid 1-dimethyl amide 4-methyl ester (1.04 g, 2.70 mmol), prepared as in step 5, and 4-ethoxy-3-nitropyridine (0.485 g, 2.89 mmol) in CH$_3$CN (10 mL) was heated at reflux for 40 hours, then at 100° C. for an amount of time sufficient to distill off the solvent. The residue was cooled to ambient temperature and dried under vacuum to give a yellow foam (1.44 g) which was used without further purification.

Step 7: 3-[(trans-1-(3-aminopyrid-4-yl)aminomethylcyclohex-4-yl)carbonyl]indole-1,4-dicarboxylic acid 1-dimethyl amide 4-methyl ester.

To a solution of 3-[(trans-1-(N-3-nitropyrid-3-yl)aminomethylcyclohex-4-yl)carbonyl]indole-1,4-dicarboxylic acid 1-dimethyl amide 4-methyl ester (0.93 g), prepared in step 6, in methanol (15mL) was added SnCl$_2$ (1.9 g, 10 mmol). Methylene chloride (5 mL) was added to give a homogeneous solution and the reaction mixture was stirred for four hours at ambient temperature. The reaction mixture was shaken with pH 7 buffer and CH$_2$Cl$_2$. The resulting emulsion was broken by filtration and the organic phase was dried over MgSO$_4$, filtered, and concentrated in vacuo to give a yellow foam which contained none of the desired product The solids from the filtration were suspended in 5% methanol/CH$_2$Cl$_2$ and shaken for 20 minutes, and filtered. The filtrate was concentrated in vacuo to give 3-[(trans-1-(3-aminopyrid-4-yl)aminomethylcyclohex-4-yl)carbonyl] indole-1,4-dicarboxylic acid 1-dimethyl amide 4-methyl ester (109 mg) as a pale-yellow foam.

Step 8: 3-{[trans-4-[(1H-2-methylimidazo[4.5-c]pyrid-1-yl) methylcyclohex-1-yl]carbonyl}indole-1,4-dicarboxylic acid 1-dimethyl amide 4-methyl ester hydrochloride.

A mixture of 3-[(trans-1-(3-aminopyrid-4-yl)aminomethylcyclohex-4-yl)carbonyl]indole-1,4-dicarboxylic acid 1-dimethyl amide 4-methyl ester (105 mg), prepared as in step 7, acetic anhydride (2 mL) and acetic acid (4 mL) was heated at 125° C. for 20 hours. The reaction mixture was cooled to ambient temperature and quenched with methanol. The solvents were removed in vacuo and the residue partitioned between CH$_2$Cl$_2$ and saturated aqueous NaHCO$_3$. The organic phase was dried over MgSO$_4$, filtered, and concentrated in vacuo to give a brown oil (68 mg). The oil was dissolved in THF (3 mL) and 4N HCl/dioxane (50 μL) was added. The resulting off-white precipitate was filtered, washed with ether, and dried in vacuo to give 3-{[trans-4-[(1H-2-methylimidazo[4.5-c]pyrid-1-yl)methylcyclohex-1-yl]carbonyl}indole-1,4-dicarboxylic acid 1-dimethyl amide 4-methyl ester hydrochloride (12 mg). $^1$H NMR (D$_3$COD, 300 MHz) δ9.19 (s, 1H), 8.57 (d, 1H), 8.39 (s, 1H), 8.26 (m, 1H), 7.75 (d, 1H), 7.43 (m, 2H), 4.35 (m, 2H), 3.80 (s, 3H), 3.01 (s, 6H), 2.82 (s, 3H), 2.81 (m, 1H), 2.02 (m, 2H), 1.77 (m, 1H), 1.48 (m, 4H), 1.24 (m, 2H). MS (DCI/NH$_3$) m/e 502 (m+H)$^+$, 244.

EXAMPLE 31

Preparation of 4-(fur-2-yl)-3-{[4-(1H-2-methylimidazo[4.5-c]pyrid-1 -yl)methylpiperidin-1-yl]carbonyl}indole-1-carboxylic acid.

Step 1: 4-bromo-3-{[4-(1H-2-methylimidazo[4.5-c]pyrid-1-yl)methylpiperidin-1 -yl]carbonyl}indole-1-carboxylic acid dimethyl amide.

The desired compound is prepared according to the method of Example 6, except substituting 4-bromoindole-3-carboxylic acid (indole 10) for 6-(4 -fluorophenyl)indole.

Step 2: 4-(fur-2-yl)-3-{[4-(1H-2-methylimidazo[4.5-c]pyrid-1-yl)methylpiperidin-1-yl]carbonyl}indole-1-carboxylic acid dimethyl amide.

The desired compound is prepared by heating a solution in dioxane of 4-bromo-3-{[4-(1H-2-methylimidazo[4.5-c]pyrid-1-yl)methylpiperidin-1-yl]carbonyl)indole-1-carboxylic acid dimethyl amide, prepared as in step 1, tri(n-butyl)-(fur-2-yl)stannane and catalytic tetrakis(triphenylphosphine)palladium(0) in a sealed tube for an amount of time sufficient to consume substantially all of the starting material, followed by cooling to ambient temperature, filtration, and chromatography on silica gel.

EXAMPLE 32

Preparation of 4-(thien-2-yl)-3-{[4-(1H-2-methylimidazo[4.5-c]pyrid-1 -yl)methylpiperidin-1-yl]carbonyl}indole-1-carboxylic acid.

The desired compound is prepared according to the method of Example 31, except substituting tri(n-butyl)-(thien-2-yl)stannane for tri(n-butyl)-(fur-2-yl)stannane.

EXAMPLE 33

Preparation of 4-ethynyl-3-{[4-(1H-2-methylimidazo[4.5-c]pyrid-1 -yl)methylpiperidin-1-yl]carbonyl}indole-1-carboxylic acid.

Step 1: 4-(trimethylsilylethynyl)-3-{[4-(1H-2-methylimidazo[4.5-c]pyrid-1-yl)methylpiperidin-1-yl]carbonyl}indole-1-carboxylic acid.

The desired compound is prepared according to the method of Example 31, except substituting trimethyl-(trimethylsilylethynyl)stannane for tri(n-butyl)-(fur-2-yl)stannane and substituting toluene for dioxane.

Step 2: 4-ethynyl-3-{[4-(1H-2-methylimidazo[4.5-c]pyrid-1-yl)methylpiperidin-1-yl]carbonyl}indole-1-carboxylic acid.

The desired compound is prepared by treating a solution in THF/CH$_3$CN of 4 -(trimethylsilylethynyl)-3-{[4-(1H-2-methylimidazo[4.5-c]pyrid-1-yl)methylpiperidin-1-yl] carbonyl}indole-1-carboxylic acid, prepared as in Example 33, with CsF at ambient temperature.

EXAMPLE 34

Preparation of 4-methoxy-3-{[4-(1H-2-methylimidazo[4.5-c]pyrid-1 -yl)methylpiperidin-1-yl]carbonyl}indole-1-carboxylic acid dimethyl amide.

The desired compound is prepared according to the method of Example 6, except substituting 4-methoxyindole-3-carboxylic acid (indole 11 ) for 6-(4-fluorophenyl)indole.

EXAMPLE 35

Preparation of 4-hydroxy-3-{[4-(1H-2-methylimidazo[4.5-c]pyrid-1 -yl)methylpiperidin-1-yl]carbonyl}indole-1-carboxylic acid dimethyl amide.

The desired compound is prepared by reaction of a solution in CH$_2$Cl$_2$ of 4-methoxy-3-{[4-(1H-2-methylimidazo[4.5-c]pyrid-1-yl)methylpiperidin-1-yl] carbonyl}indole-1-carboxylic acid dimethyl amide, prepared as in Example 34, with BBr$_3$.

EXAMPLE 36

Preparation of 4-(N,N-dimethylaminocarbonyloxy)-3-{[4-(1H-2-methylimidazo[4.5-c]pyrid-1-yl)methylpiperidin-1-yl]carbonyl}indole-1-carboxylic acid dimethyl amide The desired compound is prepared by reaction of 4-hydroxy-3-{[4-(1H-2-methylimidazo[4.5-c]pyrid-1-yl)methylpiperidin-1-yl]carbonyl}indole-1-carboxylic acid dimethyl amide, prepared as in Example 35, with NaH and dimethylcarbamyl chloride.

EXAMPLE 37

Preparation of 4-(N,N-dimethylaminocarbonylamino)-3-{[4-(1H-2-methylimidazo[4.5-c]pyrid-1-yl)methylpiperidin-1-yl]carbonyl}indole-1-carboxylic acid dimethyl amide.

Step 1: 4-(N,N-dimethylcaminocarbonylamino)indole.

The desired compound is prepared by addition to a −78° C. solution in THF of 4-aminoindole of lithium hexamethyldisilazide and dimethylcarbamyl chloride followed by warming to ambient temperature, aqueous workup, and chromatography on silica gel.

Step 2: 4-(N,N-dimethylcaminocarbonylamino)indole-3-carboxylic acid dimethyl amide.

The desired compound is prepared according to the method of Indole 1, except substituting 4-(N,N-dimethyl-caminocarbonylamino)indole, prepared as in step 1, for 6-(4-fluorophenylindole).

Step 3: 4-(N,N-dimethylaminocarbonylamino)-3-{[4-(1H-2-methylimidazo[4.5-c]pyrid-1-yl)methylpiperidin-1-yl]carbonyl}indole-1-carboxylic acid dimethyl amide.

The desired compound is prepared according to the method of Example 6, except substituting 4-(N,N-dimethylcaminocarbonylamino)indole-3-carboxylic acid dimethyl amide, prepared as in step 2, for 6-(4-fluorophenyl)indole-3-carboxylic acid dimethyl amide.

The compounds represented in Table 3 are prepared from 6-(4-fluorophenyl)-3-{[4-(1H-2-methylimidazo[4.5-c]pyrid-1-yl)methylpiperidin-1-yl]carbonyl}indole by the methods described in Examples 8 and WO 93/01813.

TABLE 3

| Example | R² |
|---|---|
| 38 | —CH₃ |
| 39 | —C(O)—O—C(CH₃)₃ |
| 40 | —C(O)—OCH₃ |
| 41 | —C(O)—O—phenyl |
| 42 | —C(O)—NH₂ |
| 43 | —C(O)—NHCH₃ |
| 44 | —C(O)—N(CH₃)(phenyl) |
| 45 | —C(O)—N(CH₃)CH₂CH₂N(CH₃)₂ |
| 46 | —C(O)—NH—CH₂CH₂—OH |

TABLE 3-continued
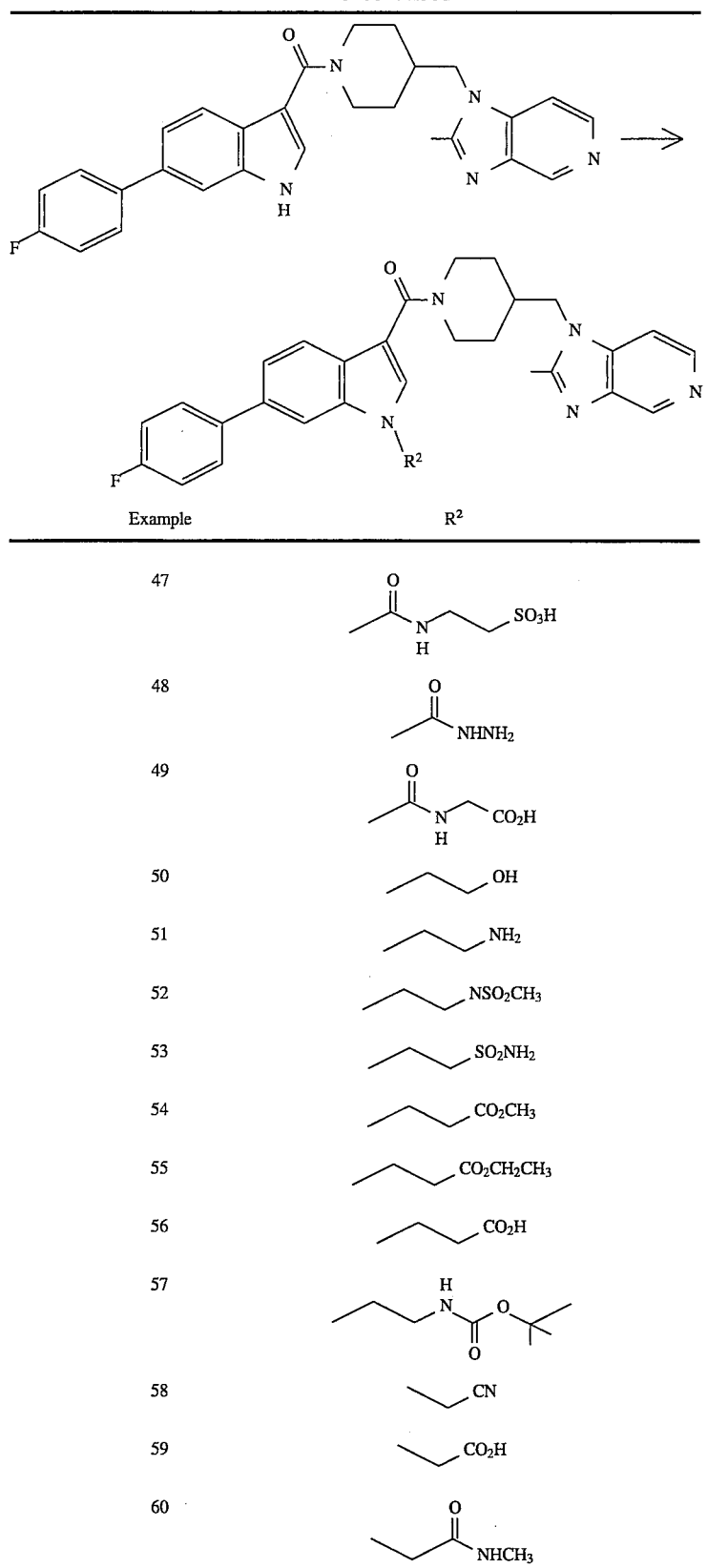
| Example | R² |
|---|---|
| 47 | CH₃C(O)NHCH₂CH₂SO₃H |
| 48 | CH₃C(O)NHNH₂ |
| 49 | CH₃C(O)NHCH₂CO₂H |
| 50 | CH₂CH₂CH₂OH |
| 51 | CH₂CH₂CH₂NH₂ |
| 52 | CH₂CH₂CH₂NSO₂CH₃ |
| 53 | CH₂CH₂CH₂SO₂NH₂ |
| 54 | CH₂CH₂CH₂CO₂CH₃ |
| 55 | CH₂CH₂CH₂CO₂CH₂CH₃ |
| 56 | CH₂CH₂CH₂CO₂H |
| 57 | CH₂CH₂CH₂NHC(O)OC(CH₃)₃ |
| 58 | CH₂CH₂CN |
| 59 | CH₂CH₂CO₂H |
| 60 | CH₂CH₂C(O)NHCH₃ |

TABLE 3-continued

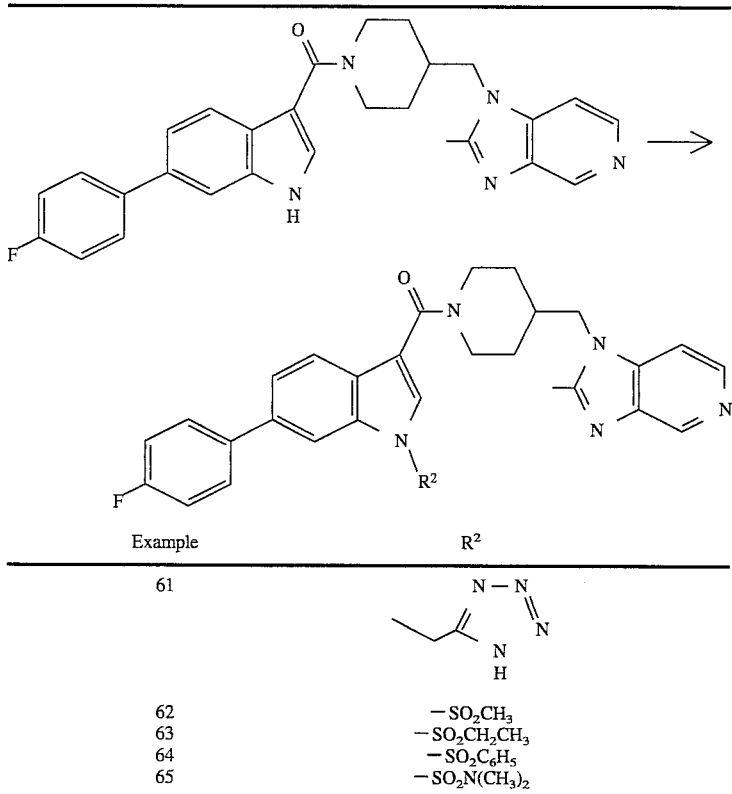

| Example | R² |
|---|---|
| 61 | (N—N=N—NH, tetrazolyl-ethylidene group shown) |
| 62 | —SO₂CH₃ |
| 63 | —SO₂CH₂CH₃ |
| 64 | —SO₂C₆H₅ |
| 65 | —SO₂N(CH₃)₂ |

We claim:

1. A compound of formula

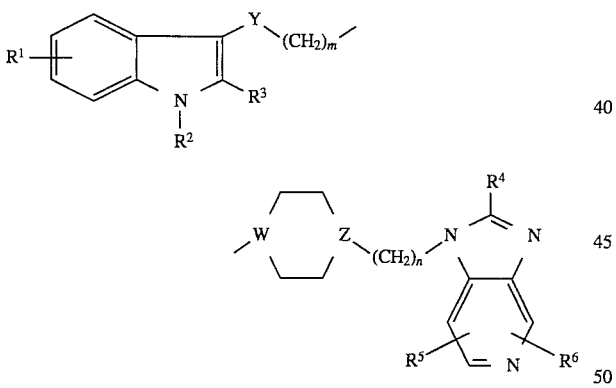

or a pharmaceutically acceptable salt thereof wherein $R^1$ is one or more groups independently selected from the group consisting of
- (a) hydrogen,
- (b) halogen,
- (c) hydroxy,
- (d) cyano,
- (e) alkyl of one to six carbon atoms,
- (f) alkenyl of two to six carbon atoms,
- (g) alkynyl of two to six carbon atoms,
- (h) alkoxy of one to six carbon atoms,
- (i) alkanoyl of one to seven carbon atoms,
- (j) —COOR⁷, wherein $R^7$ is
    - hydrogen,
    - alkyl of one to ten carbon atoms, or
    - phenylalkyl wherein the alkyl portion is of one to four carbon atoms,
- (k) unsubstituted phenyl,
- (l) phenyl, substituted with
    - alkyl of one to six carbon atoms,
    - alkoxy of one to six carbon atoms,
    - halogen,
    - —NR⁸R⁹, where $R^8$ and $R^9$ are independently selected from hydrogen and alkyl of one to six carbon atoms, or $R^8$ and $R^9$ together with the nitrogen atom to which they are attached form a pyrrolidinyl, piperidinyl, piperazinyl, or morpholinyl ring,
    - —COOR⁷,
    - —C(O)NR⁸R⁹, or
    - —SO₂NR⁸R⁹,
- (m) —C(O)NR⁸R⁹,
- (n) —OC(O)NR⁸R⁹,
- (o) —NHC(O)NR⁸R⁹,
- (p) 2- or 3-furyl,
- (q) 2- or 3-thienyl,
- (r) 2-, 4-, or 5-thiazolyl,
- (s) 2-, 3-, or 4-pyridyl,
- (t) 2-, or 4-pyrimidyl,
- (u) phenylalkyl in which the alkyl portion is of one to six carbon atoms,
- (v) phenylalkyl, in which the alkyl portion is of one to six carbon atoms and the phenyl moiety is substituted with
    - halogen,
    - alkyl of from one to six carbon atoms, or
    - alkoxy of from one to six carbon atoms,
- (w) unsubstituted benzoyl,
- (x) benzoyl substituted with
    - halogen,
    - alkyl of from one to six carbon atoms, or alkoxy of from one to six carbon atoms,
(y) unsubstituted phenoxy,
(z) phenoxy substituted with
  halogen,
  alkyl of from one to six carbon atoms, or
  alkoxy of from one to six carbon atoms,
(aa) unsubstituted phenylalkyloxy, in which the alkyl portion is of one to six carbon atoms,
(bb) phenylalkyloxy in which the alkyl portion is of one to six carbon atoms and the phenyl moiety is substituted with
  halogen,
  alkyl of from one to six carbon atoms, or
  alkoxy of from one to six carbon atoms,
(cc) unsubstituted phenylalkanoyl, in which the alkanoyl portion is of one to seven carbon atoms, and
(dd) phenylalkanoyl, in which the alkanoyl portion is of one to seven carbon atoms and the phenyl moiety is substituted with;
  halogen,
  alkyl of from one to six carbon atoms, or
  alkoxy of from one to six carbon atoms;

$R^2$ is selected from the group consisting of
(a) hydrogen,
(b) alkyl of one to six carbon atoms;
(c) —$(CH_2)_p COOR^7$, where p is 0, 1, 2, 3, or 4,
(d) —$(CH_2)_q NR^8 R^9$, where q is 2, 3, or 4,
(e) —$(CH_2)_p COR^7$
(f) —$(CH_2)_q OR^7$,
(g) —$(CH_2)_p SO_2 R^7$,
(h) —$(CH_2)_p SO_2 NR^8 R^9$,
  where $R^7$, $R^8$ and $R^9$ are as defined above,
(i) —$(CH_2)_p CONR^{10} R^{11}$, where $R^{10}$ and $R^{11}$ are independently selected from the group consisting of
  hydrogen,
  alkyl of one to six carbon atoms,
  —$(CH_2)_r COOR^7$, where r is 1, 2, 3, or 4,
  —$(CH_2)_r NR^8 R^9$,
  —$(CH_2)_r OH$,
  —$(CH_2)_r SO_2 R^7$, and
  —$(CH_2)_r SO_2 NR^8 R^9$, or
  $R^{10}$ and $R^{11}$ taken together define a pyrrolidine, morpholine, or thiomorpholine ring,
(j) —$(CH_2)_p CN$,
(k) —$(CH_2)_p$-1H-tetrazol-5-yl,
(l) —$CONHNH_2$,
(m) unsubstituted phenylalkyl wherein the alkyl portion is of one to four carbon atoms, and
(n) phenylakyl wherein the alkyl portion is of one to four carbon atoms and the phenyl moiety is substituted with
  halogen,
  alkyl of from one to six carbon atoms, or
  alkoxy of from one to six carbon atoms;

$R^3$ is selected from the group consisting of hydrogen and alkyl of one to six carbon atoms;

Y is selected from the group consisting of
  >C=O, and
  >S(O)$_t$, wherein t is 1 or 2;

W is N;

Z is CH $R^4$ is selected from the group consisting of
(a) alkyl of one to six carbon atoms,
(b) alkenyl of two to six carbon atoms,
(c) alkynyl of two to six carbon atoms,
(d) alkoxy of one to six carbon atoms,
(e) alkylthio of one to six carbon atoms,
(f) alkoxyalkyl in which the alkoxy and alkyl portions are independently of one to six carbon atoms,
(g) alkylthioalkyl in which the alkyl portions each independently of one to six carbon atoms,
(h) haloalkyl of one to six carbon atoms,
(i) unsubstituted phenylalkyl wherein the alkyl portion is of one to six carbon atoms,
(j) phenylalkyl wherein the alkyl portion io of one to six carbon atoms and the phenyl is substituted with
  alkyl of one to six carbon atoms,
  haloalkyl of one to six carbon atoms,
  alkoxy of one to six carbon atoms,
  hydroxy, or
  halogen,
(k) cycloalkyl of three to eight carbon atoms,
(l) unsubstituted thiophenyl, and
(m) thiophenyl substituted with
  alkyl of one to six carbon atoms,
  haloalkyl of one to six carbon atoms,
  alkoxy of one to six carbon atoms,
  hydroxy, or
  halogen;

$R^5$ and $R^6$ are independently selected from the group consisting of
  hydrogen,
  alkyl of one to six carbon atoms,
  halogen,
  haloalkyl, and
  alkoxy of one to six carbon atoms;

m is 0 or 1; and n is 0, 1, or 2.

2. A compound or pharmaceutically acceptable salt thereof as defined by claim 1 wherein
  $R^1$ is one or more groups independently selected from the group consisting of
    hydrogen,
    halogen,
    alkyl of one to six carbon atoms,
    alkynyl of two to four carbon atoms,
    alkoxy of one to six carbon atoms,
    unsubstituted phenyl,
    phenyl, substituted with
      alkyl of one to six carbon atoms,
      alkoxy of one to six carbon atoms,
      halogen,
    —$COOR^7$, wherein $R^7$ is hydrogen, alkyl of one to ten carbon atoms, or phenylalkyl wherein the alkyl portion is of one to four carbon atoms,
    —$C(O)NR^8 R^9$,
    —$OC(O)NR^8 R^9$,
    2- or 3-furyl, and
    2- or 3-thienyl;
  $R^3$, $R^5$ and $R^6$ are hydrogen;
  Y is >C=O or >S(O)$_2$; and
  $R^4$ is alkyl of one to six carbon atoms.

3. A compound or pharmaceutically acceptable salt thereof as defined by claim 2 wherein
  $R^2$ is selected from the group consisting of
    —$CONR^{10} R^{11}$, where $R^{10}$ and $R^{11}$ are independently selected from the group consisting of
      hydrogen,
      alkyl of one to six carbon atoms, and
    —$(CH_2)_q OR^7$, wherein q is 2, 3, or 4, and $R^7$ is alkyl of one to four carbon atoms.

4. A compound or pharmaceutically acceptable salt thereof as defined by claim 1 wherein Z is CH;

m is 0 or 1; and n is 0 or 1, provided that m and n are both not 0 or 1.

5. A compound or pharmaceutically acceptable salt thereof as defined by claim 1 selected from the group consisting of:

6-(4-fluorophenyl)-3-{(4-(1H-2-methylimidazo(4.5-c)pyrid-1-yl)piperidin-1-yl)carbonyl}indole-1-carboxylic acid dimethyl amide, 6-(4-fluorophenyl)-3-{(4-(1H-2-methylimidazo(4.5-c)pyrid-1-yl)piperidin-1-yl)carbonyl}indole, 3-{(4-(1H-2-methylimidazo(4.5-c)pyrid-1-yl)piperidin-1-yl)carbonyl}indole, 3-{(4-(1H-2-methylimidazo(4.5-c)pyrid-1-yl)piperidin-1-yl)carbonyl}indole-1,4-dicarboxylic acid 1-dimethyl amide-4-methyl ester, 3-{(4-(1H-2-methylimidazo(4.5-c)pyrid-1-yl)methylpiperidin-1-yl)carbonyl}indole-1,4-dicarboxylic acid 1-dimethyl amide-4-methyl ester, 6-(4-fluorophenyl)-3-{(4-(1H-2-methylimidazo(4.5-c)pyrid-1-yl)methylpiperidin-1-yl)carbonyl}indole-1-carboxylic acid dimethyl amide, 4-chloro-3-{(4-(1H-2-methylimidazo(4.5-c)pyrid-1-yl)methylpiperidin-1-yl)carbonyl}indole-1-carboxylic acid dimethyl amide, 1-(2-ethoxyethyl)-6-(4-fluorophenyl)-3-{(4-(1H-2-methylimidazo(4.5-c)pyrid-1-yl)methylpiperidin-1-yl)carbonyl}indole, 1-(2-ethoxyethyl)-4-chloro-3-{(4-(1H-2-methylimidazo(4.5-c)pyrid-1 -yl)methylpiperidin-1-yl)carbonyl}indole, 6-(4-fluorophenyl)-3-{(4-(1H-2-methylimidazo(4.5-c)pyrid-1-yl)piperidin-1-yl)sulfonyl}indole-1-carboxylic acid t-butyl ester, 6-(4-fluorophenyl)-3-{(4-(1H-2-methylimidazo(4.5-c)pyrid-1-yl)piperidin-1 -yl)sulfonyl}indole, 6-(4-fluorophenyl)-3-{(4-(1H-2-methylimidazo(4.5-c)pyrid-1-yl)piperidin-1-yl)sulfonyl}indole-1-carboxylic acid dimethyl amide, 6-(4-fluorophenyl)-3-{(4-(1H-2-methylimidazo(4.5-c)pyrid-1 -yl)methylpiperidin-1-yl)sulfonyl}indole-1-carboxylic acid t-butyl ester, 6-(4-fluorophenyl)-3-{(4-(1H-2-methylimidazo(4.5-c)pyrid-1-yl)methylpiperidin-1-yl)sulfonyl}indole, 6-(4-fluorophenyl)-3-{(4-(1H-2-methylimidazo(4.5-c)pyrid-1-yl)methylpiperidin-1-yl)sulfonyl}indole-1-carboxylic acid dimethyl amide, 6-(4-fluorophenyl)-3-{(4-(1H-2-methylimidazo(4.5-c)pyrid-1-yl)piperidin-1 -yl)acetyl}indole, 6-(4-fluorophenyl)-3-{(4-(1H-2-methylimidazo(4.5-c)pyrid-1-yl)piperidin-1-yl)acetyl}indole-1-carboxylic acid dimethyl amide, 3-{(4-(1H-2-methylimidazo(4.5-c)pyrid-1-yl)piperidin-1-yl)acetyl}indole-4 -carboxylic acid methy ester, 3-{(4-(1H-2-methylimidazo(4.5-c)pyrid-1-yl)piperidin-1-yl)acetyl}indole-1,4-dicarboxylic acid 1-dimethyl amide 4-methyl ester, 1-(2-ethoxyethyl)-3-{(4-(1H-2-methylimidazo(4.5-c)pyrid-1-yl)piperidin-1 -yl)acetyl}indole-1-carboxylic acid methyl ester, 4-chloro-3-{(4-(1H-2-methylimidazo(4.5-c)pyrid-1-yl)piperidin-1-yl)acetyl}indole, 1-(2-ethoxyethyl)-4-chloro-3-{(4-(1H-2-methylimidazo(4.5-c)pyrid-1-yl)piperidin-1-yl)acetyl}indole, 4-chloro-3-{(4-(1H-2-methylimidazo(4.5-c)pyrid-1-yl)piperidin-1-yl)acetyl}indole-1-carboxylic acid dimethyl amide, 4-methyl-3-{(4-(1H-2-methylimidazo(4.5-c)pyrid-1-yl)piperidin-1-yl)acetyl}indole, 1-(2-ethoxyethyl)-4-methyl-3-{(4-(1H-2-methylimidazo(4.5-c)pyrid-1-yl)piperidin-1-yl)acetyl}indole, and 4-methyl-3-{(4-(1H-2-methylimidazo(4.5-c)pyrid-1-yl)piperidin-1-yl)acetyl}indole-1-carboxylic acid dimethyl amide.

6. A pharmaceutical composition useful for inhibiting PAF in a mammal in need of such treatment comprising a PAF-inhibitive effective amount of a compound as defined by claim 1 in combination with a pharmaceutically acceptable carrier.

7. A method of inhibiting platelet activating factor comprising administering to a mammal in need of such treatment a therapeutically effective amount of a compound as defined by claim 1.

* * * * *